(12) United States Patent
Jenkins et al.

(10) Patent No.: US 9,050,589 B2
(45) Date of Patent: Jun. 9, 2015

(54) ALKENE AZIRIDINATION

(71) Applicant: University of Tennessee Research Foundation, Knoxville, TN (US)

(72) Inventors: David Matthew Jenkins, Knoxville, TN (US); Steven Alan Cramer, Knoxville, TN (US); Zheng Lu, Knoxville, TN (US)

(73) Assignee: University of Tennessee Research Foundation, Knoxville, TN (US)

(*) Notice: Subject to any disclaimer, the term of this patent is extended or adjusted under 35 U.S.C. 154(b) by 0 days.

(21) Appl. No.: 13/926,465

(22) Filed: Jun. 25, 2013

(65) Prior Publication Data

US 2013/0345431 A1 Dec. 26, 2013

Related U.S. Application Data

(60) Provisional application No. 61/663,882, filed on Jun. 25, 2012.

(51) Int. Cl.
| | |
|---|---|
| *C07F 1/10* | (2006.01) |
| *C07F 15/02* | (2006.01) |
| *B01J 31/22* | (2006.01) |
| *B01J 23/745* | (2006.01) |
| *C07D 203/14* | (2006.01) |
| *C07D 203/26* | (2006.01) |
| *C07F 17/02* | (2006.01) |

(52) U.S. Cl.
CPC ............ *B01J 31/2273* (2013.01); *C07D 203/14* (2013.01); *B01J 31/2295* (2013.01); *C07D 203/26* (2013.01); *C07F 17/02* (2013.01); *C07F 15/02* (2013.01); *C07F 1/10* (2013.01); *B01J 2231/74* (2013.01); *B01J 2531/0258* (2013.01); *B01J 2531/62* (2013.01); *B01J 2531/821* (2013.01); *B01J 2531/828* (2013.01); *B01J 2531/842* (2013.01); *B01J 2531/845* (2013.01)

(58) Field of Classification Search
CPC ............ C07F 15/00; C07F 15/02; C07F 1/10; C07D 203/14; C07D 403/14; C01J 31/2273; C01J 2231/74
See application file for complete search history.

(56) References Cited

PUBLICATIONS

Bass et al. Organometallics 2010, 29, 3235-3238.*
Cramer et al. J. Am. Chem. Soc. 2011, 133, 19342-19345 and its supporting information.*
McKie et al. Angew. Chem. Int. Ed. 2007, 46, 6525-6528 and its supporting information.*
Garrison et al. Chem. Rev. 2005, 105, 3978-4008.*
Park et al. Tetrahedron 2009, 65, 10756-10761.*

* cited by examiner

*Primary Examiner* — Matthew Coughlin
(74) *Attorney, Agent, or Firm* — Johnson, Marcou & Isaacs, LLC; Ian J. Griswold

(57) ABSTRACT

Disclosed are metal-bound tetracarbene catalysts, such as iron based aziridination catalyst, having the formula:

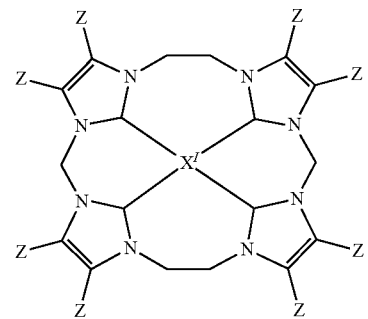

wherein X is a group 6, 7, 8, 9, or 10 metal and wherein Z is a hydrogen, alkyl, aryl or organic group, wherein the alkyl, aryl or organic group is optionally are independently substituted. In a specific example, a metal-bound tetracarbene catalyst has the formula:

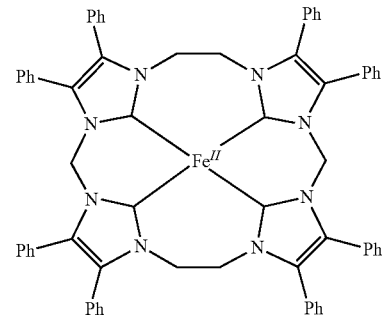

Also disclosed are methods of making (synthesizing), transmetallation reagents, these agents, metal-bound tetracarbene catalysts, and a method of catalytic alkene aziridination, using the disclosed metal-bound tetracarbene catalysts.

16 Claims, 14 Drawing Sheets

¹H NMR of 9-(*p*-tolyl)-9-azabicyclo[6.1.0]nonane $^{13}$C NMR of 9-(*p*-tolyl)-9-azabicyclo[6.1.0]nonane ¹H NMR of 2,2,3,3-tetramethyl-1-(p-tolyl)aziridine $^{13}$C NMR of 2,2,3,3-tetramethyl-1-(*p*-tolyl)aziridine

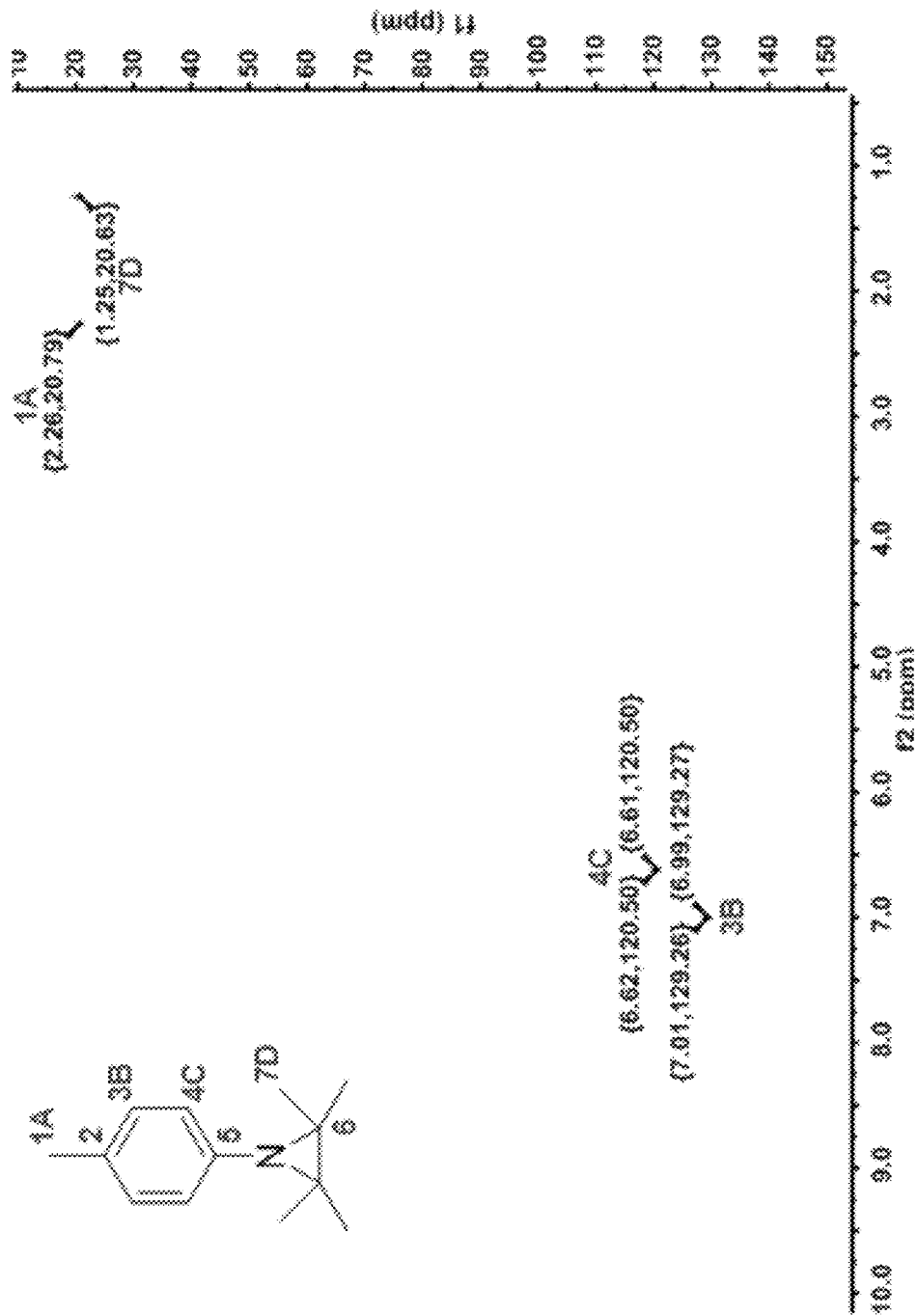
FIG. 6 HSQC of 2,2,3,3-tetramethyl-1-(p-tolyl)aziridine

ALKENE AZIRIDINATION

CROSS REFERENCE TO RELATED APPLICATION

This application claims the benefit of the earlier filing date of U.S. Provisional Application No. 61/663,882, filed Jun. 25, 2012, which is specifically incorporated herein by reference is its entirety.

FIELD

This disclosure generally relates to metal-bound tetracarbene catalysts, such as iron based aziridination catalyst, and the use of this catalyst in metal-catalyzed aziridination of alkenes.

BACKGROUND

Aziridines, the smallest nitrogen heterocyclic compounds, exhibit numerous important applications, including serving as essential motifs of biologically interesting compounds and as valuable synthons for preparation of various amine derivatives. See, for example, Hu, *Tetrahedron* 2004, 60, 2701; Sweeney, *Chem. Soc. Rev.* 2002, 31, 247; Zwanenburg et al., *Top. Curr. Chem.* 2001, 216, 93; and McCoull et al., *Synthesis* 2000, 1347. Among several approaches, metal-catalyzed asymmetric aziridination of alkenes with proper nitrene sources represents one of the most general and direct methods for construction of the three-membered ring structure. See, for example, Muller et al., *Chem. Rev.* 2003, 103, 2905; Jacobsen, In Comprehensive Asymmetric Catalysis; Jacobsen et al., Eds.; Springer: Berlin, 1999, 2, 607; and Halfen, *Curr. Org. Chem.* 2005, 9, 657.

Despite the successful development of catalytic epoxidation from alkenes over the last 30 years, the nitrogen analogue, catalytic aziridination, has languished behind. Part of the reason is the lack of nitrogenous variants of peroxides or dioxygen, which are used to form epoxides in conjunction with alkenes. Today, "$C_2+N_1$" aziridination reactions that combine an alkene and a nitrene fragment typically use iodoimine reagents such as PhI=NTs (Ts=tosylate), chloramine-T, or tosyl azide as the nitrene reagent. The disadvantage of these reactions is that the tosyl group must be removed before the desired final substituent can be placed on the ring, which reduces the atom economy and can lead to ring degradation. Organic azides are an alternative to these current nitrene reagents. Aryl azides can be easily synthesized in one step from amines and are tolerant of a wide variety of functional groups. Finally, since the correct functionality can be installed on the organic azide prior to catalysis, the use of organic azides instead of PhI=NTs should improve the atom economy of these reactions, thereby eliminating the step of removing the tosylate group before installing the desired moiety on the nitrogen atom.

A catalytic "C2+N1" aziridination that is successful with a wide variety of substrates, both for alkenes and organic azides, would be a significant advance in chemical synthesis. A very limited number of catalytic ruthenium, cobalt, and iron porphyrin systems have been developed that perform "C2+N1" aziridination with organic azides, but they are limited to strongly electron-withdrawing aryl azides (such as p-nitrophenyl azide) and/or styrene derivatives for the alkene. Thus, the need exists for a new class of aziridination catalysts that do not suffer from the above identified deficiencies. Since the aziridine functional group is found in natural products and also used in pharmaceuticals, broadening the scope of the aziridination reaction is significant.

SUMMARY

Disclosed are metal-bound tetracarbene catalysts, such as iron based aziridination catalyst, having the formula:

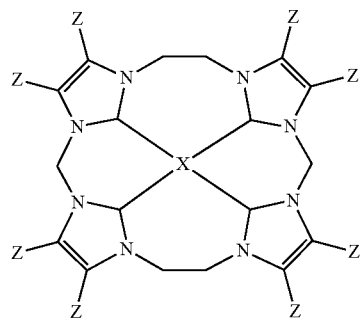

wherein X is a group 6, 7, 8, 9, or 10 metal and wherein Z is a hydrogen, alkyl, aryl or organic group, wherein the alkyl, aryl or organic group is optionally and independently substituted. In some examples, the metal is a group 8 metal selected from the group consisting of Fe, Ru, and Os. In some examples, the metal-bound tetracarbene catalyst has the formula:

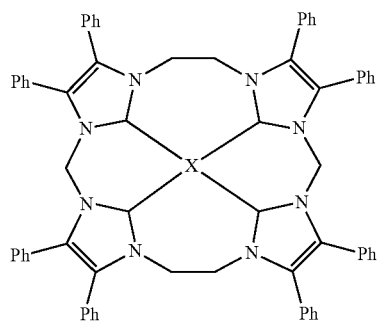

where X is a group 6, 7, 8, 9, or 10 metal and the phenyl (PH) is optionally and independently substituted. In a specific example, the metal-bound tetracarbene catalyst has the formula:

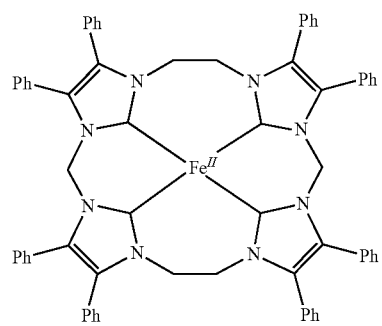

Also disclosed is a method of making a transmetallating agent, including contacting a tetraimidazolium precursor $(^{Me,Et}TC^{Ph})(X)_4$, where X is a counter ion with a silver salt Ag(X) where X is a counter ion in the presence of an organic solvent and optionally in the presence of a base, where the phenyl moieties can be independently substituted at any or all positions. Transmetallating reagents are disclosed with the general formula $[\{(^{Me,Et}TC^{Ph})Ag\}_2Ag_2](X)_4$, where X is a counter ion.

Also disclosed are methods of making (synthesizing) metal-bound tetracarbene catalysts. In some embodiments, a method of making a metal bound tetracarbene catalyst, includes contacting a transmetallating reagent $[\{(^{Me,Et}TC^{Ph})Ag\}_2Ag_2](X)_4$, where X is a counter ion, with a group 6, 7, 8, 9, or 10 metal salt in the presence of a solvent.

In other embodiments, this method includes contacting the tetraimidazolium precursor $(^{Me,Et}TC^{Ph})(I)_4$, with a strong base to deprotonate the tetraimidazolium precursor, thereby forming a deprotonated tetraimidazolium precursor, wherein the phenyl groups of the tetraimidazolium precursor are optionally substituted. The deprotonated tetraimidazolium precursor is then contacted with a solution including a group 6, 7, 8, 9, or 10 metal, such as iron. In some examples, the deprotonated tetraimidazolium precursor is further contacted with of thallium hexafluorophosphate in acetonitrile thereby forming a metal bound tetracarbene catalyst having the formula $[(^{Me,Et}TC^{Ph})X(NCCH_3)_{0-2}](PF_6)_2$, where X is the group 6, 7, 8, 9, or 10 metal. In some examples, the strong base comprises lithium diisopropylamide $(LiN^iPr_2)$.

Also disclosed are methods of catalytic alkene aziridination. The methods include treating an alkene with an optionally substituted alkyl or aryl azide in the presence of a disclosed metal bound tetracarbene catalyst, such as $[(^{Me,Et}TC^{Ph})Fe(NCCH_3)_2](PF_6)_2$. In some examples, the alkene is selected from the group consisting of aromatic alkene, non-aromatic alkene, di-substituted alkene, tri-substituted alkene, tetra-substituted alkene, cis-alkene, trans-alkene, cyclic-alkene, and non-cyclic alkene.

The foregoing and other features and advantages of the disclosure will become more apparent from the following detailed description, which proceeds with reference to the accompanying figures.

BRIEF DESCRIPTION OF THE DRAWINGS

FIGS. 3A, 3B, 4A, 4B, 5A, 5B and 6 are NMR spectra (including spectral assignment) of selected aziridinated alkenes.

DETAILED DESCRIPTION

I. Summary of Terms

Figure 1:
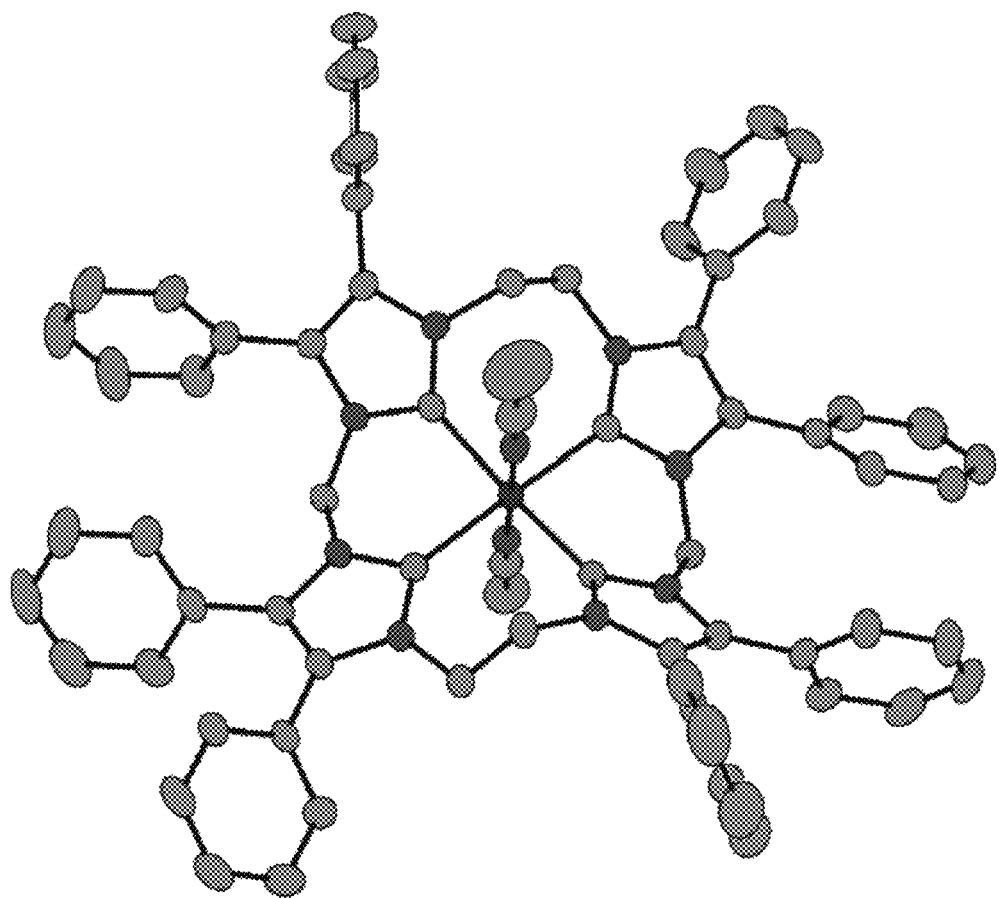
FIG. 1 is a digital image of the X-ray crystal structure of $[(^{Me,Et}TC^{Ph})Fe(NCCH_3)_2](PF_6)_2$. The ellipsoids (50% probability) represent Fe, N, and C. Counteranions, solvent molecules, and H atoms have been omitted for clarity.

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Unless otherwise noted, technical terms are used according to conventional usage. Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2).

To facilitate review of the various embodiments of the disclosure, the following explanations of specific terms are provided:

As used herein, the term "alkyl" means linear, branched, or cyclic, hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups.

The alkyl group can be optionally substituted with one or more alkyl group substituents which can be the same or different, where "alkyl group substituent" includes alkyl, halo, arylamino, acyl, hydroxy, aryloxy, alkoxyl, alkylthio, arylthio, aralkyloxy, aralkylthio, carboxy, alkoxycarbonyl, oxo and cycloalkyl. There can be optionally inserted along the alkyl chain one or more oxygen, sulfur or substituted or unsubstituted nitrogen atoms, wherein the nitrogen substituent is hydrogen, alkyl (also referred to herein as "alkylaminoalkyl"), or aryl. "Branched" refers to an alkyl group in which an alkyl group, such as methyl, ethyl or propyl, is attached to a linear alkyl chain.

The term "aryl" is used herein to refer to an aromatic substituent, which can be a single aromatic ring or multiple aromatic rings which are fused together, linked covalently, or linked to a common group such as a methylene or ethylene moiety. The common linking group can also be a carbonyl as in benzophenone or oxygen as in diphenylether or nitrogen in diphenylamine. The aromatic ring(s) can include phenyl, naphthyl, biphenyl, diphenylether, diphenylamine and benzophenone among others. In particular embodiments, the term "aryl" means a cyclic aromatic comprising about 5 to about 10 carbon atoms, including 5- and 6-membered hydrocarbon and heterocyclic aromatic rings.

The aryl group can be optionally substituted with one or more aryl group substituents which can be the same or different, where "aryl group substituent" includes alkyl, aryl, aralkyl, hydroxy, alkoxyl, aryloxy, aralkoxyl, carboxy, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene and —NR'R", where R' and R" can be each independently hydrogen, alkyl, aryl and aralkyl.

Specific examples of aryl groups include but are not limited to cyclopentadienyl, phenyl, furan, thiophene, pyrrole, pyran, pyridine, imidazole, isothiazole, isoxazole, pyrazole, pyrazine, pyrimidine, and the like.

The term "alkoxy" is used herein to refer to the —$OZ_1$ radical, where $Z_1$ is selected from the group consisting of alkyl, substituted alkyl, cycloalkyl, substituted cycloalkyl, heterocycloalkyl, substituted heterocycloalkyl, silyl groups and combinations thereof as described herein. Suitable alkoxy radicals include, for example, methoxy, ethoxy, benzyloxy, t-butoxy, and the like. A related term is "aryloxy" where $Z_1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

The term "amino" is used herein to refer to the group —$NZ_1Z_2$, where each of $Z_1$ and $Z_2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "azide" as used herein refers to the anion with the formula $N_3$—. Organic azides engage in useful organic reactions and have the general formula R—N=N=N, where R is an organic substitution. The terminal nitrogen is mildly nucleophilic. Azides easily extrude diatomic nitrogen.

A "heteroatom," as used herein, is an atom other than carbon. In some embodiments, the heteroatoms are selected from the group consisting of N, O, P, S, Si, B, Ge, Sn, and Se. In some embodiments, the heteroatoms are selected from one of N and O.

"Halide" or "halo" is defined as being selected from the group consisting of Br, Cl, I and F. In the some embodiments, the halo groups are selected from one of Br and I.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxyl, protected hydroxyl, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein alone or as part of another group denote organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, as alkaryl, alkenaryl, and alkynaryl.

The "substituted hydrocarbyl" moieties described herein, e.g., the substituted alkyl, the substituted alkenyl, the substituted alkynyl, and the substituted aryl moieties, are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substitutents include halogen, heterocyclo, alkoxy, alkenoxy, alkynoxy, aryloxy, hydroxyl, protected hydroxy, keto, acyl, acyloxy, nitro, amino, amido, nitro, cyano, thiol, ketals, acetals, esters and ethers.

III. Detailed Description of Several Embodiments

A. Introduction

Despite the numerous advances in homogeneous catalysis that have been achieved through the use of N-heterocyclic carbenes (NHCs) as auxiliary ligands, very few macrocyclic polydentate carbenes have been synthesized. As disclosed herein, the inventors have synthesized a new ligand platform based on small-ringed (16 or 18 atoms) macrocyclic tetraimidazoliums as tetra-NHC precursors. These small-ringed tetracarbene macrocycles form novel and reactive complexes on group 6, 7, 8, 9 and 10 metals. Numerous of these novel tetracarbene complexes have been characterized by the inventors using spectroscopic methods and X-ray crystallography, which demonstrates that the four carbenes bind to the metal in an equatorial configuration.

As disclosed herein, it is demonstrated that using iron and the ligand, aziridination of unactivated aliphatic alkenes with simple organic azides can be achieved. Because the aziridine functional group is found in natural products and pharmaceuticals, broadening the scope of the reaction is significant. As disclosed herein, the catalyst $[(^{Me,Et}TC^{Ph})Fe(NCCH_3)_2](PF_6)_2$ reacts with substituted azides, such as alkyl and aryl azides, and a wide variety of substituted aliphatic alkenes, including tetrasubstituted ones, to give aziridines in a $C_2+N_1$ addition reaction. Furthermore, it is demonstrated that this novel iron catalyst can be recovered and reused up to three additional times without significant reduction in yield.

B. Metal Bound Tetracarbene Catalysts

Disclosed herein is a class of metal-bound tetracarbene catalysts, which in some examples act as azirination catalysts. The metal bound tetracarbene complexes have the general formula shown below:

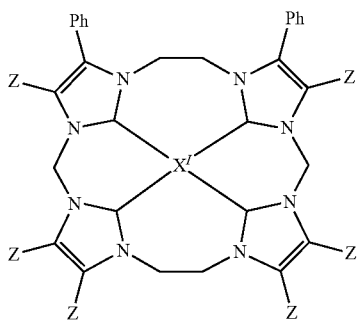

where X is a group 6, 7, 8, 9, or 10 metal, and wherein the Z is a hydrogen, alkyl, aryl or organic group, wherein the alkyl, aryl or organic group is optionally and independently substituted at any or all positions, for example with H, alkyl, aryl, alkenyl, alkynyl, aralkyl, aralkynyl, cycloalkyl, cycloalkenyl, heteroalkyl, heteroaryl, halide, alkoxy, aryloxy, alkylthio, arylthio, silyl, siloxy, or an amino groups. In some examples, the phenyl (Ph) moieties are substituted with H. In specific examples, the metal is a group 8 metal, such as iron (Fe), ruthenium (Ru), or osmium (Os). In a specific example, the metal is Fe. In some examples, the metal is a group 9 metal, such as cobalt (Co), rhodium (Rh), and iridium (Ir). In some examples, the metal is a group 10 metal, such as nickel (Ni), palladium (Pd), and platinum (Pt). In some examples, the metal is a group 7 metal, such as manganese (Mn), technetium (Tc), and rhenium (Re).

In some examples, the metal is a group 6 metal, such as chromium (Cr), molybdenum (Mo), and tungsten (W).

In some examples, the metal-bound tetracarbene catalyst has the formula:

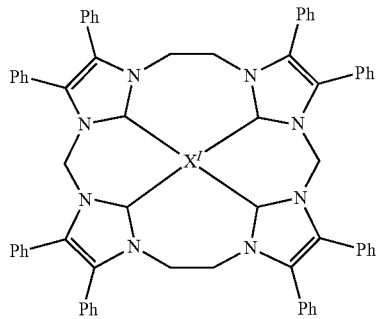

where X is a group 6, 7, 8, 9, or 10 metal and the phenyl (PH) is optionally and independently substituted, for example with H, alkyl, aryl, alkenyl, alkynyl, aralkyl, aralkynyl, cycloalkyl, cycloalkenyl, heteroalkyl, heteroaryl, halide, alkoxy, aryloxy, alkylthio, arylthio, silyl, siloxy, or an amino groups. In a specific example, the metal-bound tetracarbene catalyst has the formula:

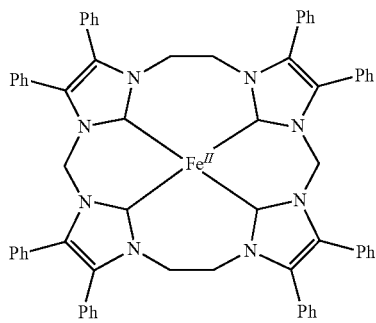

where the phenyl (PH) is optionally and independently substituted, for example with H, alkyl, aryl, alkenyl, alkynyl, aralkyl, aralkynyl, cycloalkyl, cycloalkenyl, heteroalkyl, heteroaryl, halide, alkoxy, aryloxy, alkylthio, arylthio, silyl, siloxy, or an amino groups.

In a specific embodiment, the metal bound tetracarbene catalyst is an aziridination catalyst and has the structure given below.

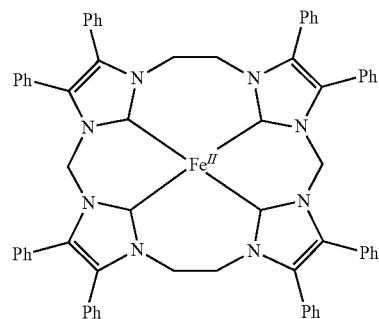

C. Methods of Making Transmetallating Reagents

Disclosed are methods of making a transmetallating reagent for use in making metal-bound tetracarbene catalysts, which in some examples act as azirination catalysts. As disclosed herein in, the development of a silver transmetallating reagent for tetracarbenes has many advantages from a synthetic perspective. Reactions with metal halide salts typically only give silver halide by-products. In contrast, using the methods disclosed herein the carbene is already formed and the reaction conditions can thus be much milder.

In some embodiments, a tetraimidazolium precursor, such as $(^{Me,Et}TC^{Ph})(X)_4$, where X is $PF_6$ or triflate (OTf) is contacted with a silver salt, such as Ag(X) where X is is $PF_6$ or triflate (OTf) in the presence of an organic solvent, such as DMSO and optionally in the presence of a base, such as N,N-diethylethanamine ($NEt_3$) or alternatively $(^{Me,Et}TC^{Ph})(X)_4$ can be reacted directly with $Ag_2O$ where the $Ag_2O$ acts as base, where the phenyl moieties can be independently substituted at any or all positions, for example with H, alkyl, aryl, alkenyl, alkynyl, aralkyl, aralkynyl, cycloalkyl, cycloalkenyl, heteroalkyl, heteroaryl, halide, alkoxy, aryloxy, alkylthio, arylthio, silyl, siloxy, or an amino groups. Bases which are useful are alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, alkali metal and alkaline earth metal phosphates, primary, secondary and tertiary amines, alkali metal and alkaline earth fluorides, and ammonium fluorides. In some embodiments, the bases include but are not limited to n-BuLi, $LiN^iPr_2$, $KN(TMS)_2$, $NaNH_2$, NaOH, NaOAc, KOt-Bu, NaOt-Bu, $Cs_2CO_3$, $K_2CO_3$, $K_3PO_4$, carbonate-containing compounds, and phosphate-containing compounds. In specific embodiments, the base is $NEt_3$. Suitable solvents include for example, ethers (e.g., diethyl ether, dimethoxymethane, diethylene glycol, dimethyl ether, tetrahydrofuran (THF), dioxane, diisopropyl ether, tert-butyl methyl ether), hydrocarbons (e.g., hexane, iso-hexane, heptane, cyclohexane, benzene, toluene, xylene), alcohols (e.g., methanol, ethanol, 1-propanol, 2-propanol, ethylene glycol, 1-butanol, 2-butanol, tert-butanol), ketones (e.g., acetone, ethyl methyl ketone, iso-butyl methyl ketone), amides (e.g., dimethylformamide, dimethylacetamide, N-methylpyrrolidone), nitriles (e.g., acetonitrile, propionitrile, butyronitrile), sulfoxides and mixtures thereof. In some embodiments, the solvent is DMSO. In some examples, the reaction is carried out for between about 1 and about 200 hours, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 minutes, 1 hour, 2 hours, 3 hours, 5 hours 10 hours, 20 hours, 50 hours or about 200 hours, or even longer in some cases. In some examples, the mixture is stirred or otherwise mixed at a temperature from about 0° C. to 200° C., such as about 30° C. to about 150° C., about 60° C. to about 120° C., about 75° C. to about 110° C., or about 85° C. to about 95° C., for example at about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., about 155° C., about 160° C., about 165° C., about 170° C., about 175° C., about 180° C., about 185° C., about 190° C., about 195° C., or about 200° C. Also disclosed are transmetallating agents, such as trasmetallating reagents produced by the disclosed methods. In some examples, the transmetallating reagent is $[\{(^{Me,Et}TC^{Ph})Ag\}_2Ag_2](X)_4$, where X is a counter ion. In specific examples, the transmetallating reagent is $[\{(^{Me,Et}TC^{Ph})Ag\}_2Ag_2](OTf)_4$. In other examples, the transmetallating reagent is $[\{(^{Me,Et}TC^{Ph})Ag\}_2Ag_2](PF_6)_4$.

In a specific embodiment, the transmetallating agent is synthesized according to the scheme set forth below as scheme 4.

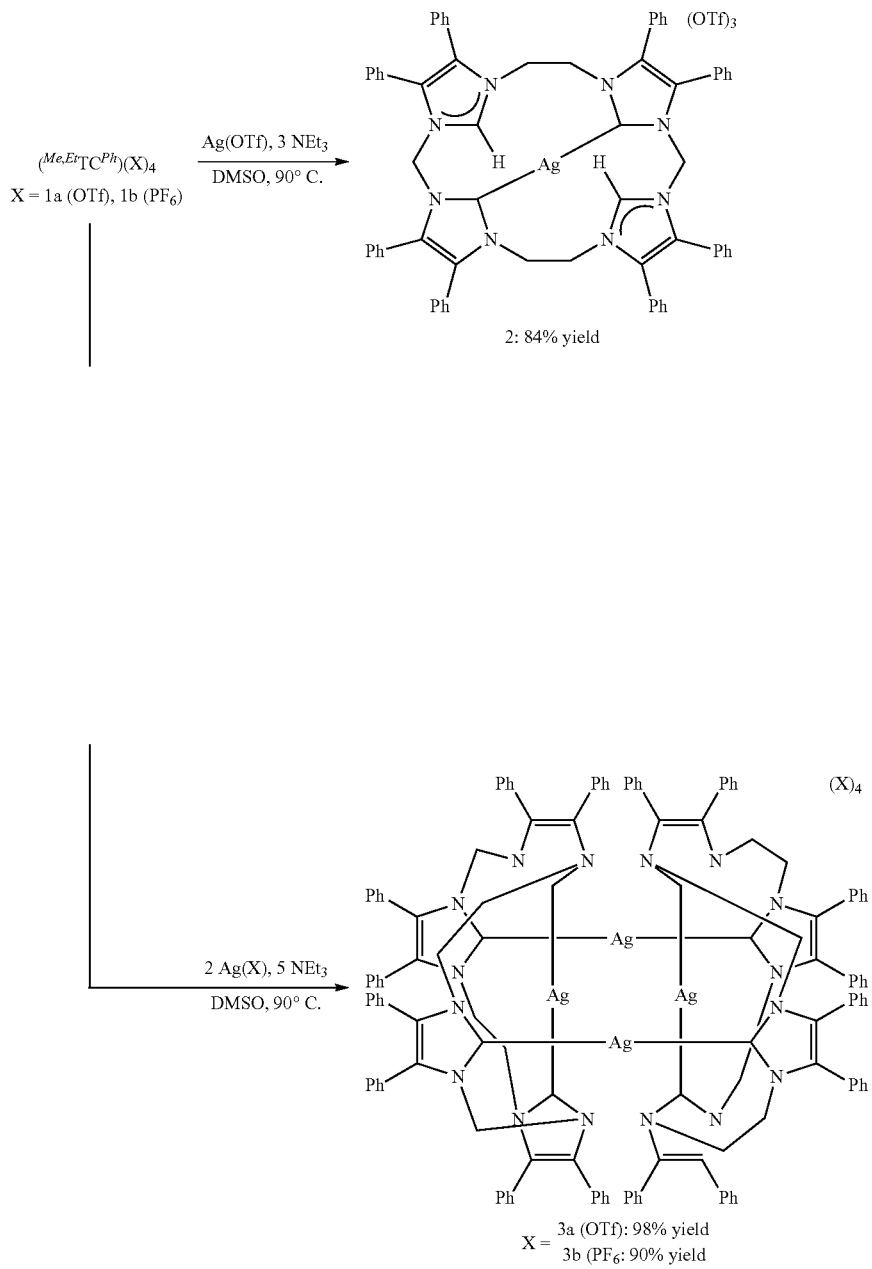

D. Methods of Making Metal Bound Tetracarbene Catalysts

Disclosed are methods of making metal-bound tetracarbene catalysts, which in some examples act as azirination catalysts, for example methods are disclosed for preparing macrocyclic tetracarbenes with first, second and third row transition metals from both sides of the periodic table by utilizing a dimeric silver transmetallating reagent.

As disclosed herein, the inventors have synthesized a dimeric silver N-heterocyclic carbine transmetallating reagent that reacts with a wide variety of divalent metal halides to give monomeric tetracarbene complexes. These silver reagents transmetallate N-heterocyclic carbenes to metal salts in moderate to high yield. All of the metal tetracarbene complexes were structurally characterized by single crystal X-ray diffraction as well as ESI-MS and other spectroscopic techniques. Since there are two $Ag^I$ ions per macrocyclic ligand, it was believed that the preferred metal salts for transmetallation reactions would be divalent metals with two halides.

In some embodiments, the transmetallating reagent $[\{(^{Me,Et}TC^{Ph})Ag\}_2Ag_2](X)_4$, where X is a counter ion, such as OTf or $PF_6$, is contacted with a metal salt such as a result of a divalent metal in the presence of a solvent, such as a mixture of THF and $CH_2CL_2$, where the phenyl moieties can be independently substituted at any or all positions, for example with H, alkyl, aryl, alkenyl, alkynyl, aralkyl, aralkynyl, cycloalkyl, cycloalkenyl, heteroalkyl, heteroaryl, halide, alkoxy, aryloxy, alkylthio, arylthio, silyl, siloxy, or an amino groups. Suitable solvents include for example, ethers (e.g., diethyl ether, dimethoxymethane, diethylene glycol, dimethyl ether, tetrahydrofuran (THF), dioxane, diisopropyl ether, tert-butyl methyl ether), hydrocarbons and substituted hydrocarbons (e.g., hexane, iso-hexane, heptane, cyclohexane, benzene, toluene, xylene), alcohols (e.g., methanol, ethanol, 1-propanol, 2-propanol, ethylene glycol, 1-butanol, 2-butanol, tert-butanol), ketones (e.g., acetone, ethyl methyl ketone, iso-butyl methyl ketone), amides (e.g., dimethylformamide, dimethylacetamide, N-methylpyrrolidone), nitriles (e.g., acetonitrile, propionitrile, butyronitrile), sulfoxides and mixtures thereof. In some embodiments, the solvent is a mixture of THF and $CH_2CL_2$. In some embodiment, the metal is a group 6, 7, 8, 9, or 10 metal, such as Fe, Ru, Cr, Mo, Os, Co, Rh, Ir, Ni, Pd, or Pt. In a specific example, the metal is Fe, such as iron(II). In some examples, the reaction is carried out for between about 1 and about 200 hours, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 minutes, 1 hour, 2 hours, 3 hours, 5 hours 10 hours, 20 hours, 50 hours or about 200 hours, or even longer in some cases. In some examples, the mixture is stirred or otherwise mixed at a temperature from about 0° C. to 200° C., such as about 30° C. to about 150° C., about 60° C. to about 120° C., about 75° C. to about 110° C., or about 85° C. to about 95° C., for example at about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., about 155° C., about 160° C., about 165° C., about 170° C., about 175° C., about 180° C., about 185° C., about 190° C., about 195° C., or about 200° C. In specific examples, the metal bound tetracarbene catalyst is synthesized according to the scheme set forth below as scheme 5, where L is the ligand for the metal M.

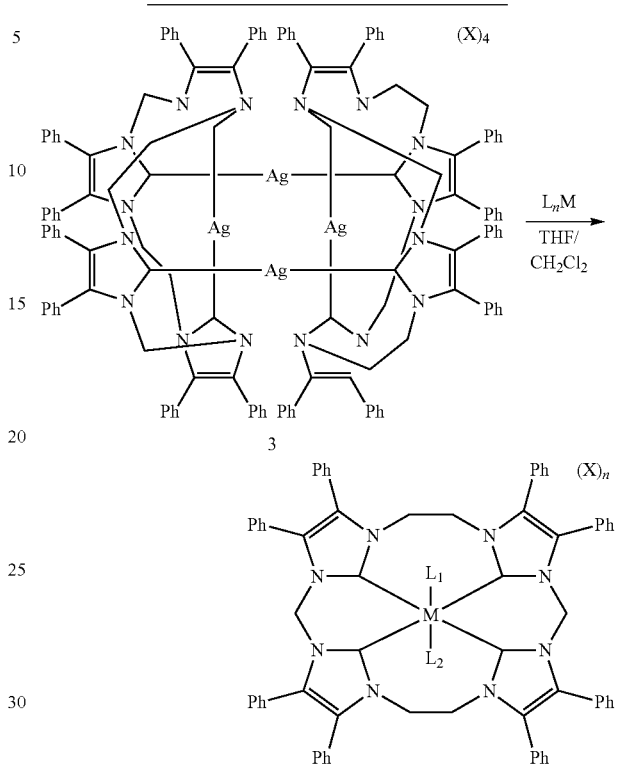

Scheme 5. Synthesis of metal complexes from $[\{(^{Me,Et}TC^{Ph})Ag\}_2Ag_2](X)_4$ In alternative embodiments for making a metal-bound tetracarbene catalyst, a tetraimidazolium precursor, such as $(^{Me,Et}TC^{Ph})(I)_4$ is reacted with a strong base, such as lithium diisopropylamide ($LiN^iPr_2$), to deprotonate the tetraimidazolium precursor, for example in the presence of an organic solvent, such as tetrahydrofuran (THF), where the phenyl moieties can be independently substituted at any or all positions, for example with H, alkyl, aryl, alkenyl, alkynyl, aralkyl, aralkynyl, cycloalkyl, cycloalkenyl, heteroalkyl, heteroaryl, halide, alkoxy, aryloxy, alkylthio, arylthio, silyl, siloxy, or an amino groups. Bases which are useful are alkali metal and alkaline earth metal hydroxides, alkali metal and alkaline earth metal carbonates, alkali metal hydrogen carbonates, alkali metal and alkaline earth metal acetates, alkali metal and alkaline earth metal alkoxides, alkali metal and alkaline earth metal phosphates, primary, secondary and tertiary amines, alkali metal and alkaline earth fluorides, and ammonium fluorides. In some embodiments, the bases include but are not limited to n-BuLi, $LiN^iPr_2$, $KN(TMS)_2$, $NaNH_2$, NaOH, NaOAc, KOt-Bu, NaOt-Bu, $Cs_2CO_3$, $K_2CO_3$, $K_3PO_4$, carbonate-containing compounds, and phosphate-containing compounds. In specific embodiments, the strong base is $LiN^iPr_2$. Suitable solvents include for example, ethers (e.g., diethyl ether, dimethoxymethane, diethylene glycol, dimethyl ether, tetrahydrofuran (THF), dioxane, diisopropyl ether, tert-butyl methyl ether), hydrocarbons (e.g., hexane, iso-hexane, heptane, cyclohexane, benzene, toluene, xylene), alcohols (e.g., methanol, ethanol, 1-propanol, 2-propanol, ethylene glycol, 1-butanol, 2-butanol, tert-butanol), ketones (e.g., acetone, ethyl methyl ketone, iso-butyl methyl ketone), amides (e.g., dimethylformamide, dimethylacetamide, N-methylpyrrolidone), nitriles (e.g., acetonitrile, propionitrile, butyronitrile), and mixtures thereof. In some embodiments, the solvent is THF. In some examples, the reaction is carried out for between about 1 and about 200 hours, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 minutes, 1 hour, 2 hours, 3 hours, 5 hours 10 hours, 20 hours, 50 hours or about 200 hours, or even longer in some cases. In some examples, the mixture is stirred or otherwise mixed at a temperature from about 0° C. to 200° C., such as about 30° C. to about 150° C. The resulting mixture is then reacted with a solution of a group 6, 7, 8, 9, or 10 metal, such as Cr, Mo, Fe, Ru, Os, Co, Rh, Ir, Ni, Pd, or Pt in an organic solvent, such as THF. In a specific example, the metal is Fe, such as iron(II). In some embodiments, addition of the solvated solution of a group 6, 7, 8, 9, or 10 metal is followed by the addition of thallium hexafluorophosphate in a organic solvent, such as acetonitrile, which gives the octahedral complex $[(^{Me,Et}TC^{Ph})X(NCCH_3)_{0-2}](PF_6)_2$, where X is the group 6, 7, 8, 9, or 10 metal. In some embodiments, addition of the solvated solution of a group 6, 7, 8, 9, or 10 metal is followed by the addition of $PF_6$ and/or OTf in a organic solvent, such as acetonitrile, DMSO, THF or combinations thereof. Suitable solvents include for example, ethers (e.g., diethyl ether, dimethoxymethane, diethylene glycol, dimethyl ether, tetrahydrofuran (THF), dioxane, diisopropyl ether, tert-butyl methyl ether), hydrocarbons (e.g., hexane, iso-hexane, heptane, cyclohexane, benzene, toluene, xylene), alcohols (e.g., methanol, ethanol, 1-propanol, 2-propanol, ethylene glycol, 1-butanol, 2-butanol, tert-butanol), ketones (e.g., acetone, ethyl methyl ketone, iso-butyl methyl ketone), amides (e.g., dimethylformamide, dimethylacetamide, N-methylpyrrolidone), nitriles (e.g., acetonitrile, propionitrile, butyronitrile), and mixtures thereof. In some embodiments, the solvent is acetonitrile. In some examples, the reaction is carried out for between about 1 and about 200 hours, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 minutes, 1 hour, 2 hours 3 hours 5 hours 10 hours, 20 hours, 50 hours 100 hours, or about 200 hours, or even longer is some cases. In some examples, the mixture is stirred or otherwise mixed at a temperature from about 0° C. to 200° C., such as about 30° C. to about 150° C.

In a specific embodiment, the metal bound tetracarbene catalyst is $[(^{Me,Et}TC^{Ph})Fe(NCCH_3)_2](PF_6)_2$ and is synthesized according to the scheme set forth below as scheme 1.

Scheme 1. Synthesis of $[(^{Me,Et}TC^{Ph})Fe(NCCH_3)_2](PF6)_2$ $(^{Me,Et}TC^{Ph})(I)_4$ + LiN$^i$Pr$_2$ $\xrightarrow{\text{1. FeI}_2, \text{THF} \\ \text{2. TIPF}_6, \text{CH}_3\text{CN}}$

1

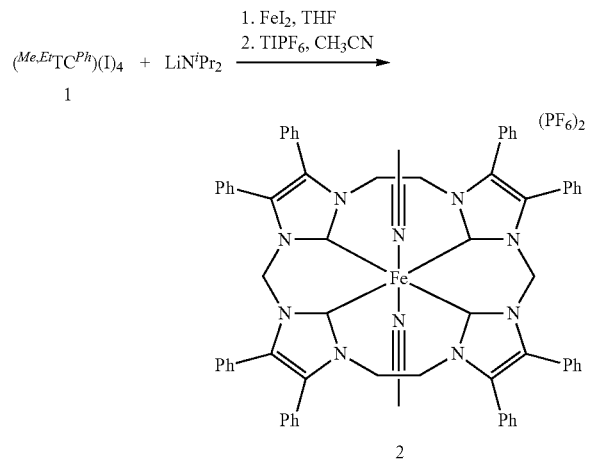

2

After the reaction is complete, the catalyst can be obtained as solid and separated off by filtration. The crude product can be freed of the solvent or the solvents and is subsequently purified by methods known to those skilled in the art and matched to the respective product, e.g. by recrystallization, distillation, sublimation, zone melting, melt crystallization or chromatography.

As disclosed herein, spectroscopic characterization of $[(^{Me,Et}TC^{Ph})Fe(NCCH_3)_2](PF_6)_2$ was consistent with a tetracarbene complex. Electrospray ionization mass spectrometry (ESI-MS) analysis of $[(^{Me,Et}TC^{Ph})Fe(NCCH_3)_2](PF_6)_2$ showed a peak at m/z 506.2 associated with $[(^{Me,Et}TC^{Ph})Fe^{2+}$ and another at m/z 1157.3 associated with $\{[(^{Me,Et}TC^{Ph})Fe(PF_6)]\}^+$, both with the correct isotopic ratios. $^1$H NMR analysis demonstrated that the acetonitrile ligands on $[(^{Me,Et}TC^{Ph})Fe(NCCH_3)_2](PF_6)_2$ exchange in $CD_3CN$ solution, since $[(^{Me,Et}TC^{Ph})Fe(NCCH_3)_2](PF_6)_2$ crystallized from $CH_3CN$ solution showed peaks only for unbound acetonitrile. $^{13}$C NMR analysis showed a resonance for the carbene carbon at 196.65 ppm, consistent with other $Fe^{II}$ N-heterocyclic carbene (NHC) complexes. In addition, complex $[(^{Me,Et}TC^{Ph})Fe(NCCH_3)_2](PF_6)_2$ was found to be air-stable in the solid state.

The X-ray crystal structure of $[(^{Me,Et}TC^{Ph})Fe(NCCH_3)_2](PF_6)_2$ shows that the acetonitrile ligands are bound in the solid state (FIG. 1), giving an octahedral complex. The average Fe—C bond distance is 2.01 Å. The trans C—Fe—C angles are 169.7 and 172.2°, demonstrating that there is only a minimal distortion about the equatorial plane formed by the macrocycle.

E. Methods of Alkene Aziridination

Disclosed are methods of catalytic alkene aziridination. In general, the methods include treating an alkene with a substituted azide, such as an optionally substituted alkyl or aryl azide, in the presence of a disclosed metal bound tetracarbene catalyst, such as $[(^{Me,Et}TC^{Ph})Fe(NCCH_3)_2](PF_6)_2$. Advantageously, the catalytic system of the present disclosure is operationally simple and capable of aziridinating both aromatic and aliphatic alkenes under mild conditions, forming the corresponding aziridines in high yields.

Organic azides, such as aryl azides, are an alternative to current nitrene reagents. Organic azides, such as aryl azides, can be easily synthesized in one step from amines and are tolerant of a wide variety of functional groups. Finally, since the correct functionality can be installed on the organic azide prior to catalysis, the use of organic azides instead of PhI=NTs should improve the atom economy of these reactions, thereby eliminating the step of removing the tosylate group before installing the desired moiety on the nitrogen atom. A catalytic "C2+N1" aziridination that is successful with a wide variety of substrates, both for alkenes and organic azides, is a significant advance in chemical synthesis.

In some embodiments, a disclosed metal bound tetracarbene catalyst, such as $[(^{Me,Et}TC^{Ph})Fe(NCCH_3)_2](PF_6)_2$ and the alkene is added to a reaction vessel. The reaction mixture is heated and stirred for a period of time prior to the addition of the organic azide. In some examples, the reaction mixture is stirred or otherwise mixed between about 1 minute and about 200 hours, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 minutes, 1 hour, 2 hours, 3 hours 5 hours 10 hours, 20 hours, 50 hours, 100 hours, 150 hours, or about 200 hours, or even longer is some cases at a temperature from about 0° C. to 200° C., such as about 30° C. to about 150° C. The organic azide is then added to the reaction and allowed to stir or otherwise mix at a designated temperature. In some examples, the reaction mixture is stirred or otherwise mixed between about 1 minute and about 200 hours, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 minutes, 1 hour, 2 hours, 3 hours 5 hours 10 hours, 20 hours, 50 hours, 100 hours, 150 hours, or about 200 hours, or even longer is some cases at a temperature from about 0° C. to 200° C., such as about 30° C. to about 150° C. Once the reaction is complete, for example as determined by GC/MS, the mixture can be removed from heat and the catalyst filtered away, for example over Celite. The catalyst can be recollected for re-use by adding acetonitrile to the filter and collecting the solution.

In general, the olefin is aziridinated with an azide source, such as a substituted azide. In some examples, the substituted azide has the formula N=N=N—$R_5$, where $R_5$ can be a carbocyclic or heterocyclic ring, hydrogen, hydrocarbyl, substituted hydrocarbyl, or heterocyclo, aryl or substituted aryl; for example, phenyl or substituted phenyl wherein the phenyl substituents are selected from the group consisting of alkyl, alkoxy, halo, trihalomethyl, acyloxy, and nitro, alkyl, alkoxy, halo, trihalomethyl, acyloxy, and nitro, an electron withdrawing group.

As disclosed herein, compounds containing an ethylenic bond, commonly known as alkenes or olefins, are aziridinated. In general, the alkene may be any of a wide range of alkenes. In some embodiments, the alkene is selected from the group consisting of aromatic alkene, non-aromatic alkene, di-substituted alkene, tri-substituted alkene, tetra-substituted alkene, cis-alkene, trans-alkene, cyclic-alkene, and non-cyclic alkene. In some embodiments, the alkene is styrene. In one embodiment, the alkene corresponds to the following structure:

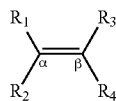

wherein $R_1$ and $R_2$ are substituents of the α-carbon of the ethylenic bond, and $R_3$ and $R_4$ are substituents of the β-carbon of the ethylenic bond. In some embodiments, $R_1$, $R_2$, $R_3$ and $R_4$ are independently hydrogen, hydrocarbyl, substituted hydrocarbyl, substituted heterocyclo, alkyl, substituted alkyl, acyl, —C(O)R, —C(O)OR, or —C(O)N$R_a R_b$, aryl or substituted aryl or heterocyclic ring, or. In one embodiment, at least two of $R_1$, $R_2$, $R_3$ and $R_4$ are a carbocyclic or heterocyclic ring, hydrogen, hydrocarbyl, substituted hydrocarbyl, or heterocyclo, aryl or substituted aryl; for example, phenyl or substituted phenyl wherein the phenyl substituents are selected from the group consisting of alkyl, alkoxy, halo, trihalomethyl, acyloxy, and nitro, alkyl, alkoxy, halo, trihalomethyl, acyloxy, and nitro, an electron withdrawing group. In some examples, $R_3$, $R_4$ and the α-carbon form a carbocyclic or heterocyclic ring. In some examples, $R_2$, $R_4$, the α-carbon, and the β-carbon form a carbocyclic or heterocyclic ring. In some examples, $R_2$, $R_3$, the α-carbon, and the β-carbon form a carbocyclic or heterocyclic ring.

To determine the best catalytic reaction conditions for aziridination with an electron-donating aryl azide, a series of test reactions were run with p-tolyl azide, 1-decene, and 2. The best results were obtained by using a 0.1 mol % catalyst loading of [($^{Me,Et}$TC$^{Ph}$)Fe(NCCH$_3$)$_2$](PF$_6$)$_2$ with a 29-fold excess of alkene and no additional solvent (Scheme 2).

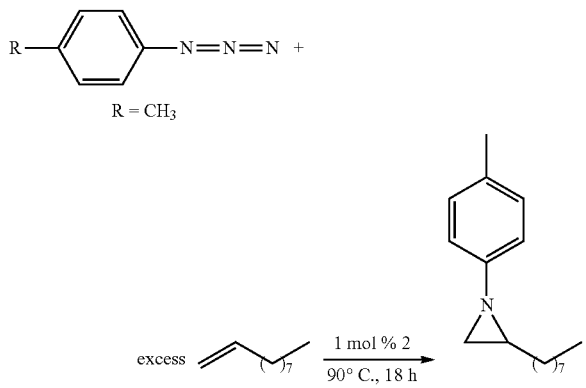

Scheme 2. Sample Aziridination Reaction

After 18 h at 90° C., the reaction was complete (all of the organic azide had reacted), and the reaction mixture was cooled to room temperature and the catalyst removed by filtration over Celite. Removal of the remaining organics under reduced pressure followed by column chromatography yielded pure 2-octyl-(p-tolyl)aziridine in 70% isolated yield (Table 1, entry 1). The identity of the product was determined by $^1$H and $^{13}$C NMR spectroscopy, GC-MS, and high-resolution MS. Increasing the catalyst loading to 1% (entry 2) improved the isolated yield to 82%. One advantage of this methodology is the ease of catalyst separation from the product, since [($^{Me,Et}$TC$^{Ph}$)Fe(NCCH$_3$)$_2$](PF$_6$)$_2$ is insoluble in the reaction mixture at room temperature.

To test the effectiveness of the catalytic system, additional azides and alkenes were evaluated (Table 1).

TABLE 1

Aziridination Reactions with [($^{Me, Et}$TC$^{Ph}$)Fe(NCCH$_3$)$_2$](PF$_6$)$_2$ as the Catalyst

| Entry | Alkene | Azide R-group | Catalyst Loading | Temp. (° C.) | Time (h) | Aziridine | Yield[a] |
|---|---|---|---|---|---|---|---|
| 1 | 1-decene | CH$_3$ | 0.1% | 90 | 18 | p-tolyl | 70%[b] |
| 2 | 1-decene | CH$_3$ | 1% | 90 | 18 | p-tolyl | 82%[b] |

TABLE 1-continued

Aziridination Reactions with [($^{Me, Et}TC^{Ph}$)Fe(NCCH$_3$)$_2$](PF$_6$)$_2$ as the Catalyst

| Entry | Alkene | Azide R-group | Catalyst Loading | Temp. (°C.) | Time (h) | Aziridine | Yield[a] |
|---|---|---|---|---|---|---|---|
| 3 | 1-octene | CF$_3$ | 0.1% | 90 | 18 | (structure with CF$_3$-phenyl aziridine, pentyl chain) | 37%[b] |
| 4 | cis-cyclooctene | CH$_3$ | 0.1% | 90 | 12 | p-tolyl (bicyclic aziridine) | 97% |
| 5 | trans-4-octene | CH$_3$ | 1% | 90 | 144 | p-tolyl (aziridine with two propyl groups) | 30%[b] |
| 6 | 1-methyl-cyclohexene | CH$_3$ | 1% | 90 | 144 | p-tolyl (methyl bicyclic aziridine) | 39%[b] |
| 7 | 2,3-dimethyl-2-butene | CH$_3$ | 0.1% | 70 | 160 | p-tolyl (tetramethyl aziridine) | 20%[b] |

[a] Isolated yields.
[b] Required chromatography.

The catalyst successfully performed aziridination with 1-octene and electron withdrawing azides such as 1-azido-4-(trifluoromethyl)benzene (entry 3) with a slightly higher yield than for previously reported Ru-porphyrin systems. Disubstituted

TABLE 2

Aziridination reaction re-using 2 with cis-cyclooctene.

| Run | Azide | Catalyst Loading | Temp. (°C.) | Time (h) | Aziridine | Yield[a] |
|---|---|---|---|---|---|---|
| 1 | p-tolylazide | 0.1% | 90 | 12 | See Table 1, Entry 4 | 97% |
| 2 | p-tolylazide | 0.1% | 90 | 12 | See Table 1, Entry 4 | 95% |
| 3 | p-tolylazide | 0.1% | 90 | 12 | See Table 1, Entry 4 | 97% |
| 4 | p-tolylazide | 0.1% | 90 | 12 | See Table 1, Entry 4 | 89% |

[a] all reported yields are isolated yields.

alkenes, including cis- and trans-substituted examples, were both successful (entries 4 and 5, respectively). The yield for 9-(p-tolyl)-9-azabicyclo[6.1.0]nonane (entry 4) was almost quantitative (97% yield) with just 0.1% catalyst loading. The reaction with trans-4-octene (entry 5) was much slower and lower-yielding, possibly because of the steric bulk of the propyl groups. Furthermore, tri- and tetrasubstituted alkenes such as 1-methylcyclohexane and 2,3-dimethyl-2-butene (entries 6 and 7, respectively) were successful. The reaction with 2,3-dimethyl-2-butene was run at 70° because of its lower boiling point, which may have contributed to the lower yield.

In contrast, others have reported that trisubstituted alkenes did not react with aryl azides and a Ru-porphyrin catalyst. Likewise, previous examples of similar tetrasubstituted aziridines have been prepared only by photolysis of electron-withdrawing organic azides to make the free nitrene prior to reaction with the alkene. In these two cases (entries 6 and 7), we have catalyzed the first examples of "$C_2+N_1$" aziridinations involving those classes of alkenes and an aryl azide. Since the catalyst [($^{Me,Et}TC^{Ph}$)Fe(NCCH$_3$)$_2$](PF$_6$)$_2$ is insoluble in the reaction mixture at room temperature, we believed that it could be recovered and reused once the catalysis was complete. Since the reaction with ciscyclooctene (Table 1, entry 4) gave the best yield with low catalyst loading, the reaction was repeated three times with the same batch of catalyst. The results demonstrated that the catalyst is reusable for this reaction with only a negligible decrease in yield by the fourth run (see Table 2).

In addition to improving the atom economy of the reaction by using alkyl and aryl azides, the ability to reuse the catalyst without significant loss of yield is quite beneficial. On the basis of previously studied aziridination reactions with aryl azides, a potential intermediate in this reaction mechanism is an iron(IV) imide, 3 (Scheme 3).

found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Synthesis of Transmetallating Reagents and Metal Bound Tetracarbene Catalysts

The synthesis of the macrocyclic tetraimidazolium ($^{Me,Et}TC^{Ph}$)(OTf)$_4$ has previously been demonstrated (see Bass et al., *Organometallics* 2010, 29, 3235-3238, which is specifically incorporated herein it its entirety). Addition of one equivalent of Ag(OTf) (silver trifluoromethanesulfonate) plus NEt$_3$ (N,N-diethylethanamine) in DMSO at 90° C. gave the monomeric silver complex [($^{Me,Et}TC^{Ph}$)(H)$_2$Ag](OTf)$_3$ in 84% yield (see Scheme 4). Like many silver NHC complexes,

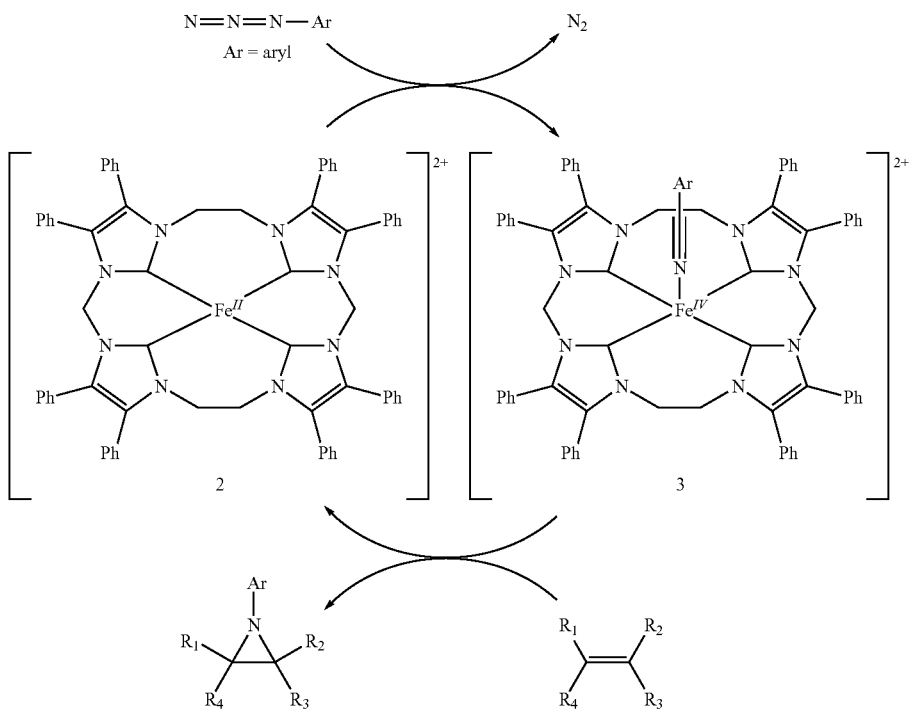

Scheme 3. Proposed Reaction Mechanism for the Aziridination

Figure 2:
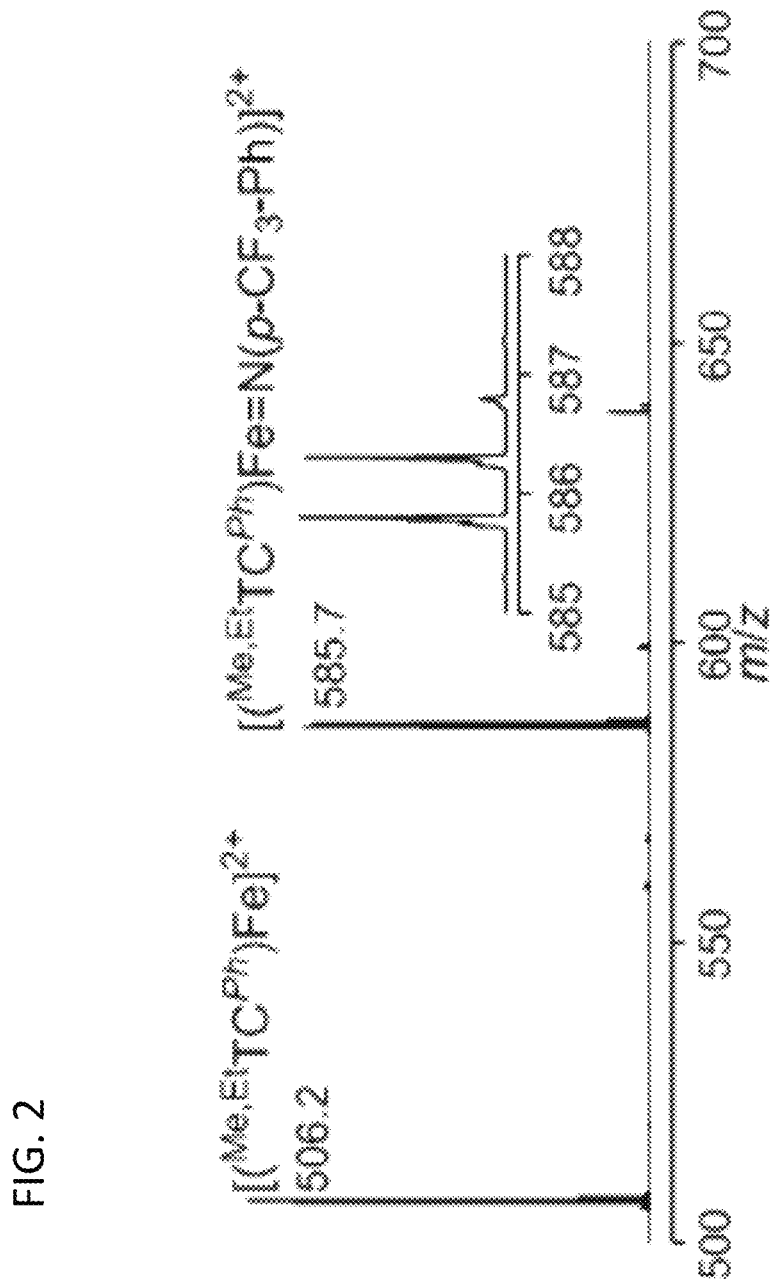
FIG. 2 is an exemplary ESI-MS spectrum measured for an acetonitrile solution of $[(^{Me,Et}TC^{Ph})Fe=N(p-CF_3-Ph)](PF_6)_2$. The inset shows the highlight for the $[(^{Me,Et}TC^{Ph})Fe=N(p-CF_3-Ph)]^{2+}$ ion.
Figure 3A:
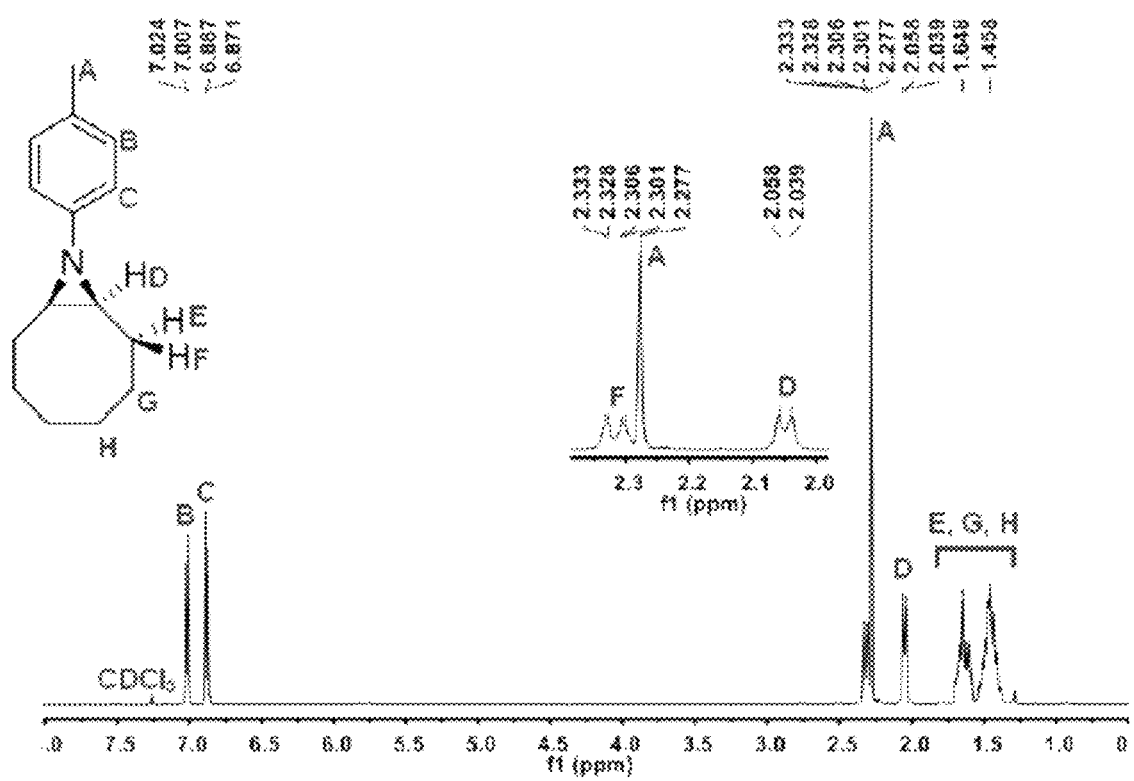
Figure 3B:
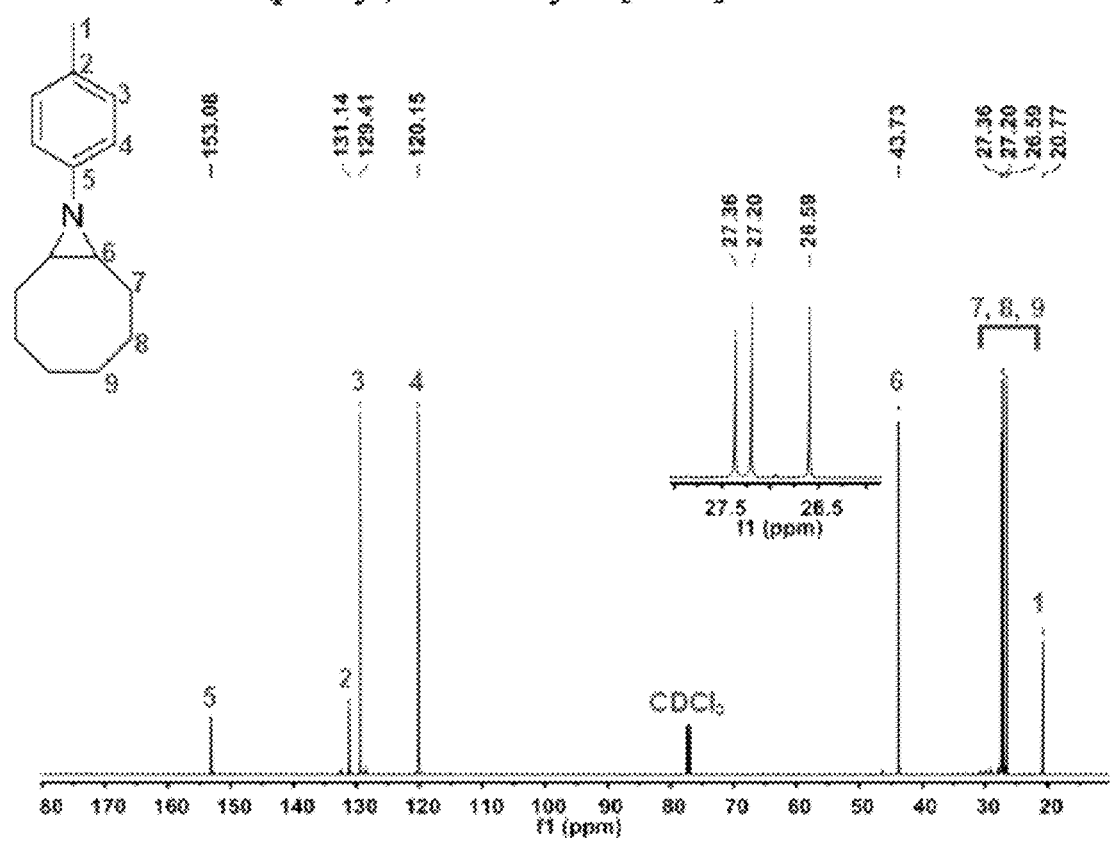

Threefold-symmetric strong σ-donor ligands have been demonstrated to stabilize iron imides in the 2+, 3+, and 4+ oxidation states, but these complexes do not react with alkenes to give aziridines, the ESIMS data are consistent with its formation. Addition of 1-azido-4-(trifluoromethyl)benzene to a solution of 2 at room temperature in acetonitrile gave an ESI-MS spectrum with a peak at 585.7 m/z associated with [($^{Me,Et}TC^{Ph}$)FedN(p-CF$_3$Ph)]$^{2+}$ (FIG. 2).

Figure 4A:
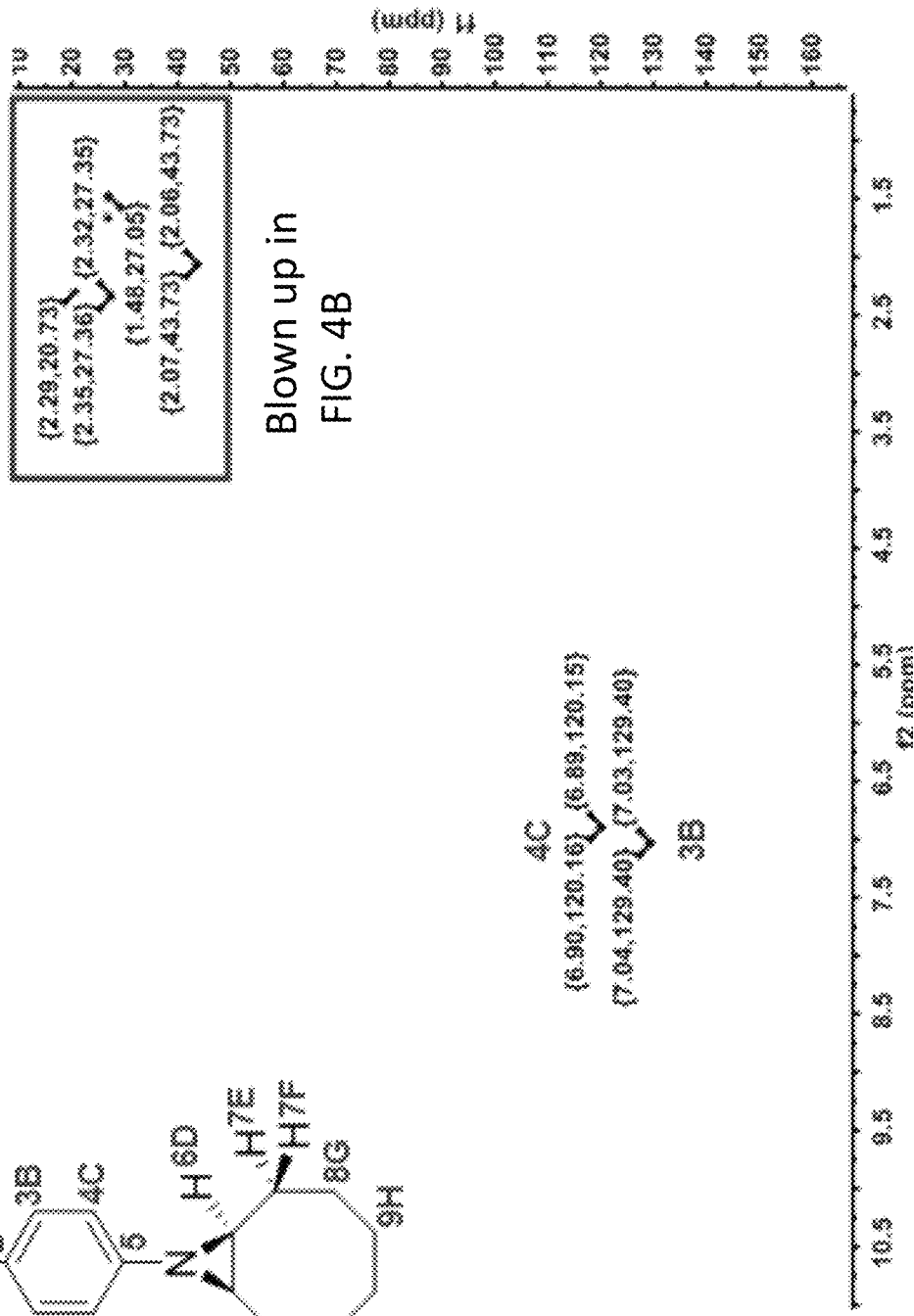
Figure 4B:
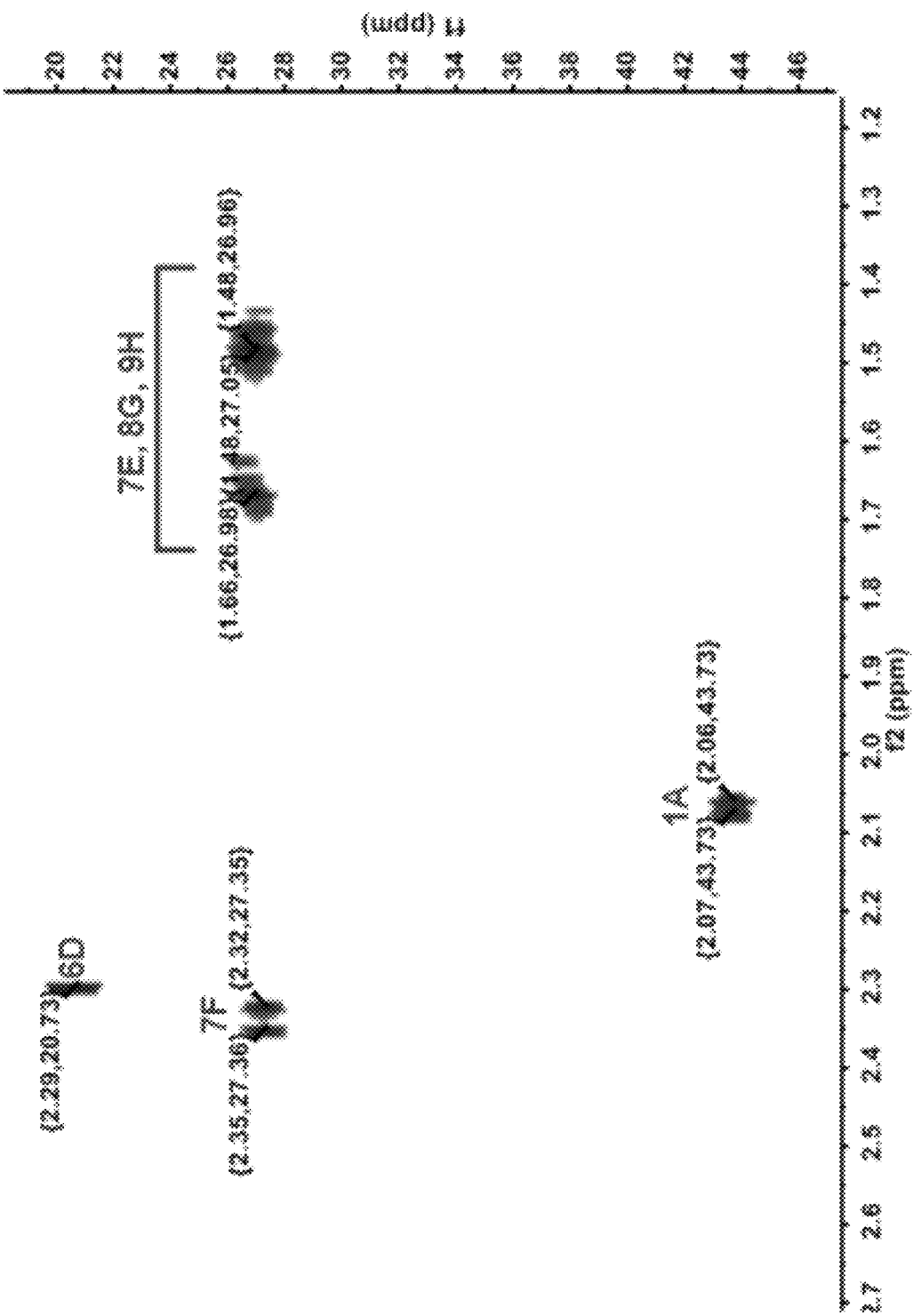
Figure 5A:
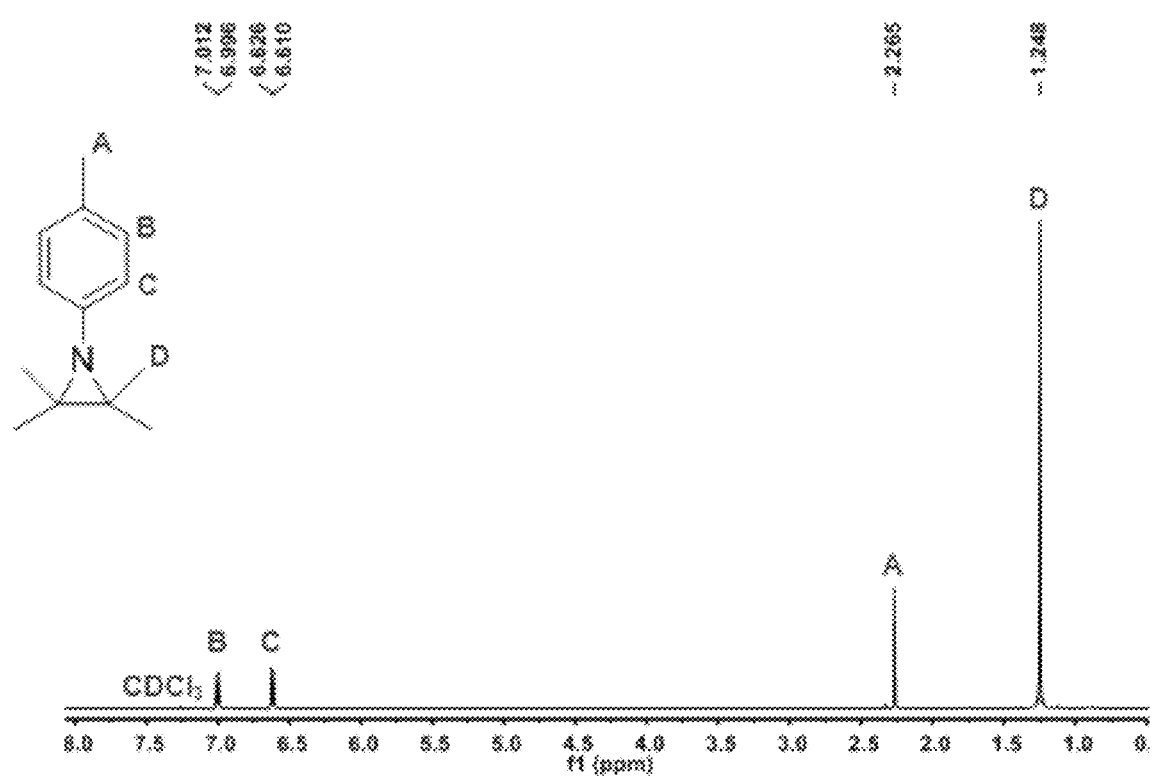
Figure 5B:
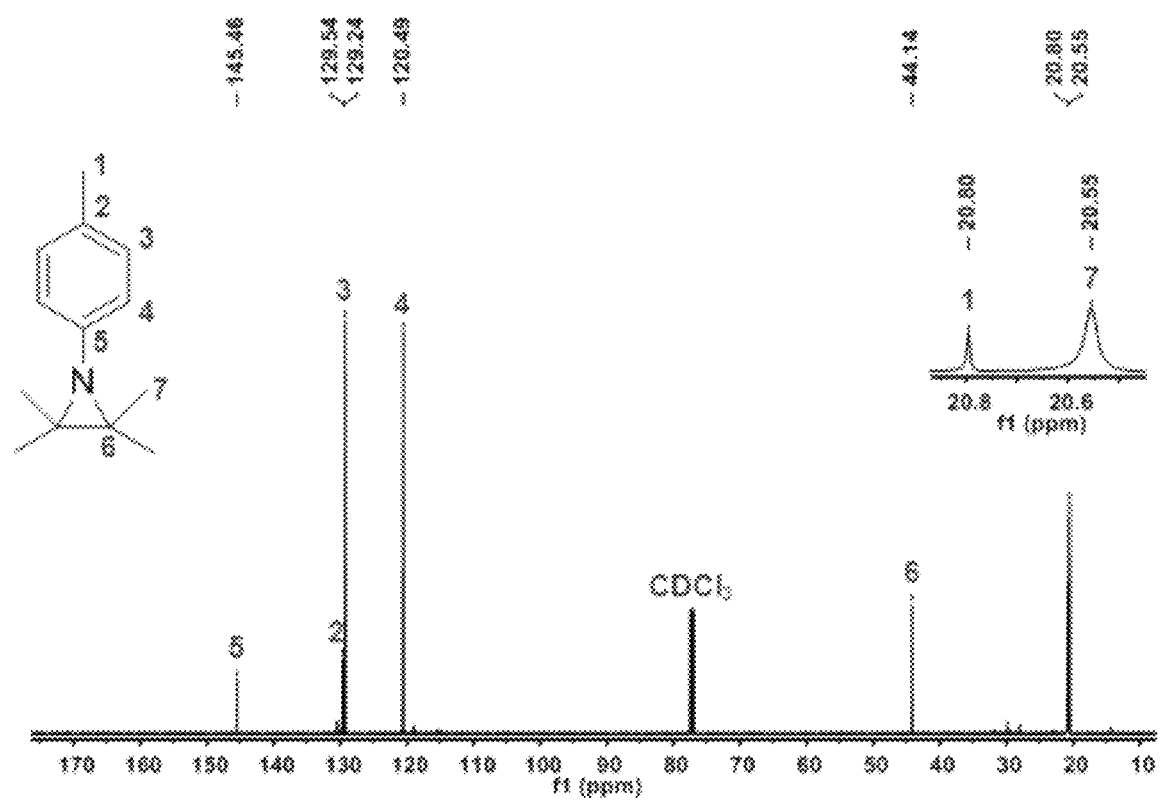

The following non-limiting examples are provided to further illustrate the present invention. It should be appreciated by those of skill in the art that the techniques disclosed in the examples that follow represent approaches the inventors have the metal ion is two coordinate which leaves two unreacted imidazoliums on the macrocycle. In the solid state, the two imidazolium hydrogens are pointed in the same direction (FIG. 4) which led to the conclusion that it would be possible to deprotonate these imidazoliums to give a dimeric carbene complex. Indeed, addition of two equivalents of Ag(X) plus NEt$_3$ to ($^{Me,Et}TC^{Ph}$)(X)$_4$ at 90° C. in DMSO yielded the dimeric silver complex [{($^{Me,Et}TC^{Ph}$)Ag}$_2$Ag$_2$](X)$_4$, (Scheme 4).

Spectroscopic characterization of [{($^{Me,Et}TC^{Ph}$)Ag}$_2$Ag$_2$](Otf)$_4$ was consistent with this novel dimeric structure. Electrospray ionization mass spectrometry (ESI-MS) analysis of

Figure 8:
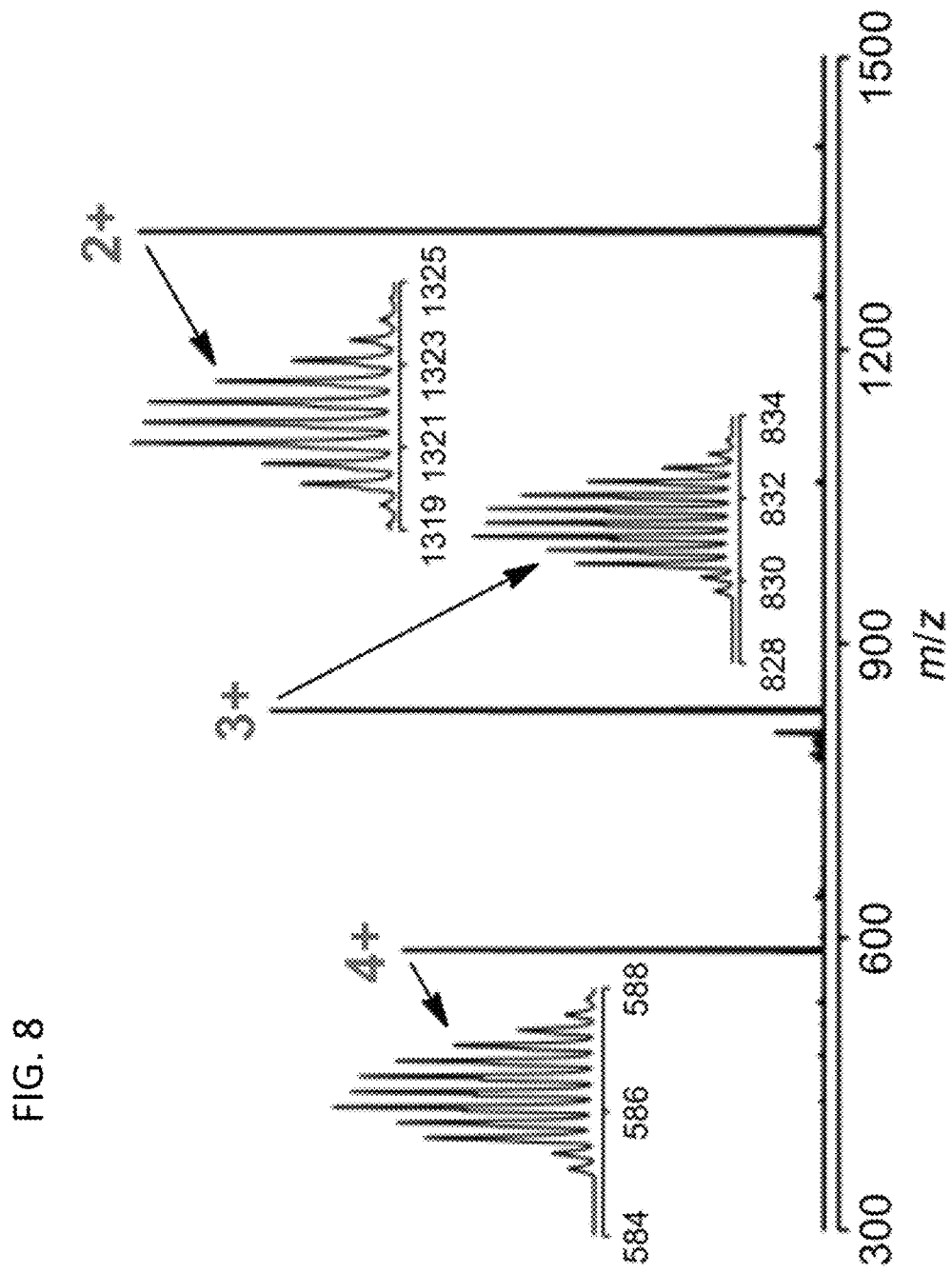
FIG. 8 shows an example electrospray ionization mass spectrum measured for an acetonitrile solution of $[\{(^{Me,Et}TC^{Ph})Ag\}_2Ag_2](OTf)_4$ (3a). The insets show highlights for the $[\{(^{Me,Et}TC^{Ph})Ag\}_2Ag_2]^{4+}$, $\{[\{(^{Me,Et}TC^{Ph})Ag\}_2Ag_2](OTf)\}^{3+}$, and $\{[\{(^{Me,Et}TC^{Ph})Ag\}_2Ag_2](OTf)_2\}^{2+}$ ions, which are denoted as "4+", "3+", and "2+", respectively.

[{($^{Me,Et}$TC$^{Ph}$)Ag}$_2$Ag$_2$](OTf)$_4$ showed peaks at m/z 586.07 associated with [{($^{Me,Et}$TC$^{Ph}$)Ag}$_2$Ag$_2$]$^{4+}$, 831.08 associated with {[{($^{Me,Et}$TC$^{Ph}$)Ag}$_2$Ag$_2$](OTf)}$^{3+}$, and 1321.10 associated with {[{($^{Me,Et}$TC$^{Ph}$)Ag}$_2$Ag](OTf)$_2$}$^{2+}$ (FIG. 8). $^{13}$C NMR for [{($^{Me,Et}$TC$^{Ph}$)Ag}$_2$Ag$_2$](OTf)$_4$ shows two resonances for the carbene carbons at 183.18 and 176.96 ppm. Interestingly, these two peaks are both split into pairs of doublets due to the coupling to both $^{107}$Ag and $^{109}$Ag. By comparing the $^{13}$C NMR of [($^{Me,Et}$TC$^{Ph}$)(H)$_2$Ag](OTf)$_3$ which only has a resonance at 178.38 ppm for the carbene carbon, it was concluded that the carbene bound to the bridging silver gives the peak at 183.18 ppm in [{($^{Me,Et}$TC$^{Ph}$)Ag}$_2$Ag$_2$](Otf)$_4$. The $^{13}$C NMR and the ESI-MS demonstrate that [{($^{Me,Et}$TC$^{Ph}$)Ag}$_2$Ag$_2$](OTf)$_4$ maintains its geometry in solution. Similar results were obtained for [{($^{Me,Et}$TC$^{Ph}$)Ag}$_2$Ag$_2$](PF$_6$)$_4$. Finally, complexes [{($^{Me,Et}$TC$^{Ph}$)Ag}$_2$Ag$_2$](Otf)$_4$ and [{($^{Me,Et}$TC$^{Ph}$)Ag}$_2$Ag$_2$](PF$_6$)$_4$ are stable in air in the solid state and in solution.

Figure 7:
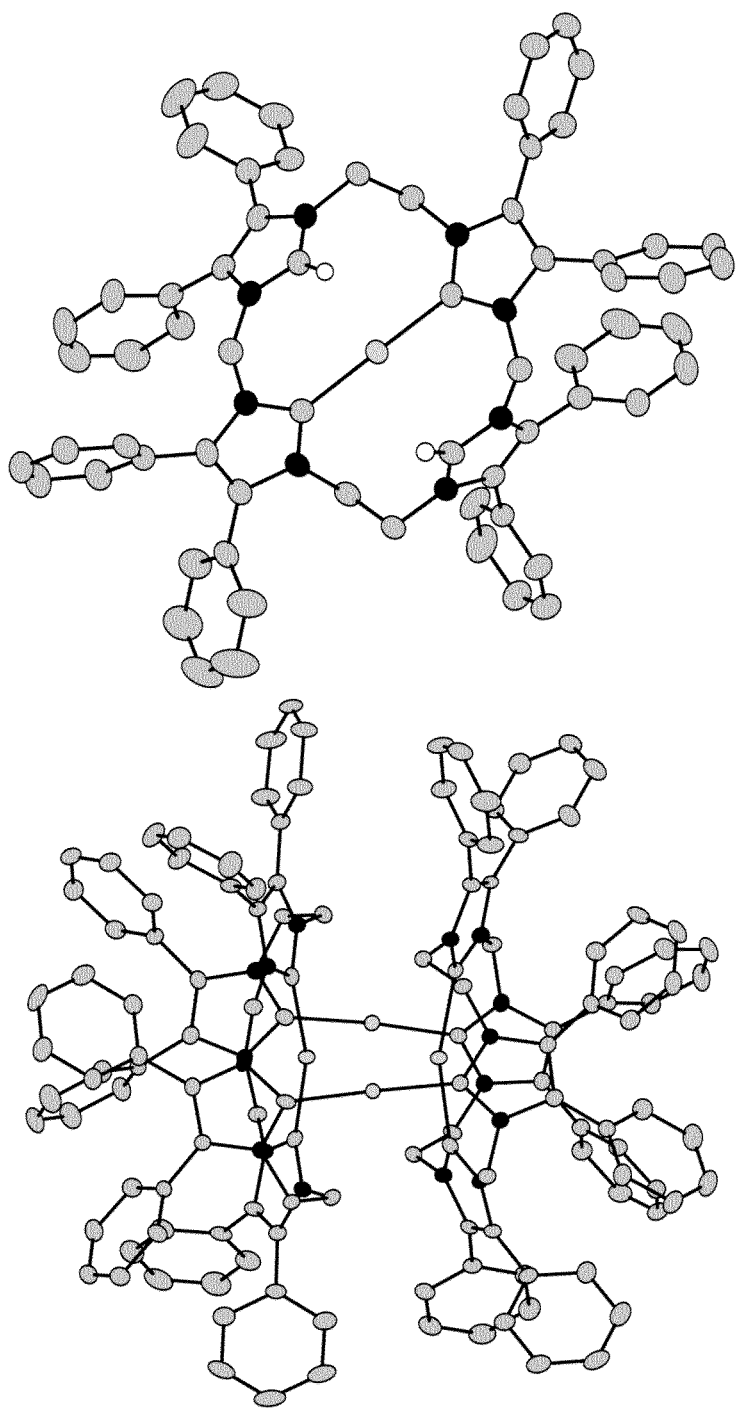
FIG. 7 shows the X-ray crystal structures of $[(^{Me,Et}TC^{Ph})(H)_2Ag](OTf)_3$ (2, top) and $[\{(^{Me,Et}TC^{Ph})Ag\}_2Ag_2](PF_6)_4$ (3b, bottom). Ellipsoids (50% probability) represent Ag, N, C, and H, respectively. Counteranions, solvent molecules and H atoms (excluding imidazolium H's) have been omitted for clarity.

The X-ray crystal structure of [{($^{Me,Et}$TC$^{Ph}$)Ag}$_2$Ag$_2$](PF$_6$)$_4$ shows the dimeric structure of the tetrasilver complex (FIG. 7). The intramolecular C—Ag—C bond angles are 161.8 and 162.7°, while the intermolecular C—Ag—C bond angles are 170.0° and 173.3°. These relatively linear bond angles suggest that there is little distortion due to the size of the macrocycle. The intramolecular Ag—C bond distances average 2.14 Å while the intermolecular Ag—C bond distances average 2.09 Å. The bond distances and angles are typical for two coordinate Ag—NHC complexes.

Since there are two Ag$^I$ ions per macrocyclic ligand, it was believed that the preferred metal salts for transmetallation reactions would be divalent metals with two halides. To canvas the periodic table, it was decided to use commercially available divalent metal salts with particular attention paid to metals which had few examples of NHCs prepared via silver transmetallation. Addition of [{($^{Me,Et}$TC$^{Ph}$)Ag}$_2$Ag$_2$](X)$_4$ these metal salts in a 50/50 mixture of THF and CH$_2$Cl$_2$ yielded five examples of macrocyclic tetracarbene complexes in moderate to high yield (Scheme 5 and Table 3). In each case, the tetracarbene ligand binds to the four sites in the equatorial plane around the metal.

TABLE 3

Transmetallation results for metal complexes from reaction shown in Scheme 5.

| Complex | L$_n$M | M | L$_1$ | L$_2$ | (X)$_n$ | Yield |
|---|---|---|---|---|---|---|
| 4 | Pt(NCPh)$_2$Cl$_2$ | Pt | — | — | (OTf)$_2$ | 93% |
| 5 | FeI$_2$ | Fe | CH$_3$CN | CH$_3$CN | (PF$_6$)$_2$ | 92%$^a$ |
| 6 | Ru(DMSO)$_4$Cl$_2$ | Ru | DMSO | DMSO | (OTf)$_2$ | 40%$^b$ |
| 7 | CoCl$_2$ | Co | OTf | — | OTf | 68% |
| 8 | CrCl$_2$ | Cr | Cl | Cl | PF$_6$ | 58%$^c$ |

Figure 11:
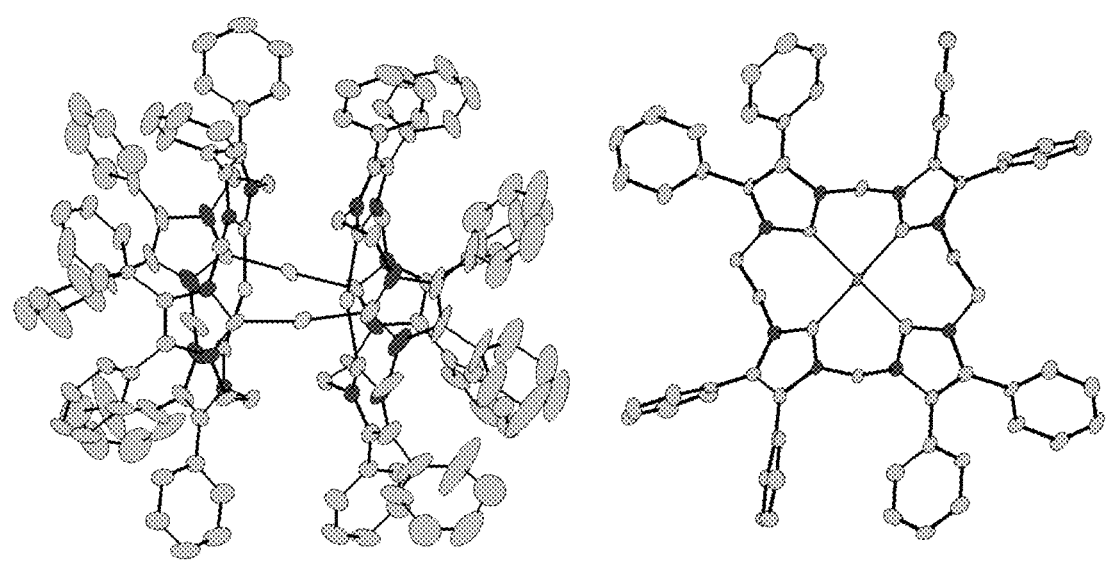
FIG. 11 shows X-ray crystal structures of $[\{(^{Me,Et}TC^{Ph})Ag\}_2Ag_2](OTf)_4$ (3a, above left) and $[(^{Me,Et}TC^{Ph})Pt](OTf)_2$ (4, above right). Ellipsoids (50% probability) represent Ag, Pt, N, and C, respectively. Counteranions, solvent molecules and H atoms have been omitted for clarity.

$^a$CH$_3$CN added during work-up prior to crystallization
$^b$Reaction heated to 60° C.
$^c$Excess CrCl$_2$ used in reaction The platinum complex, [($^{Me,Et}$TC$^{Ph}$)Pt](Otf)$_2$ (4 in Table 3), is similar to a complex described previously but with a different counteranion (PF$_6$ previously). The X-ray structure for [($^{Me,Et}$TC$^{Ph}$)Pt](Otf)$_2$ is shown in FIG. 11. While the imidazolium deprotonation approach with NEt$_3$ led to a 7% isolated yield, transmetallation led to a 93% yield of [($^{Me,Et}$TC$^{Ph}$)Pt](Otf)$_2$. Similar results were obtained for the iron complex, [($^{Me,Et}$TC$^{Ph}$)Fe(NCCH$_3$)$_2$](PF$_6$)$_2$ (5 in Table 3), which was synthesized in 92% yield. While [($^{Me,Et}$TC$^{Ph}$)Fe(NCCH$_3$)$_2$](PF$_6$)$_2$ has been demonstrated to be an excellent aziridination catalyst (see the Examples below) one of the limitations of this catalyst's development was that it could only be synthesized in 11% yield using an in situ deprotonation of the imidazoliums with lithium diisopropyl amide (alternative method of synthesis). In the iron case, this is the second example of a tetracarbene on iron and the second case of successful transmetallation of an NHC to iron from silver.

Figure 9:
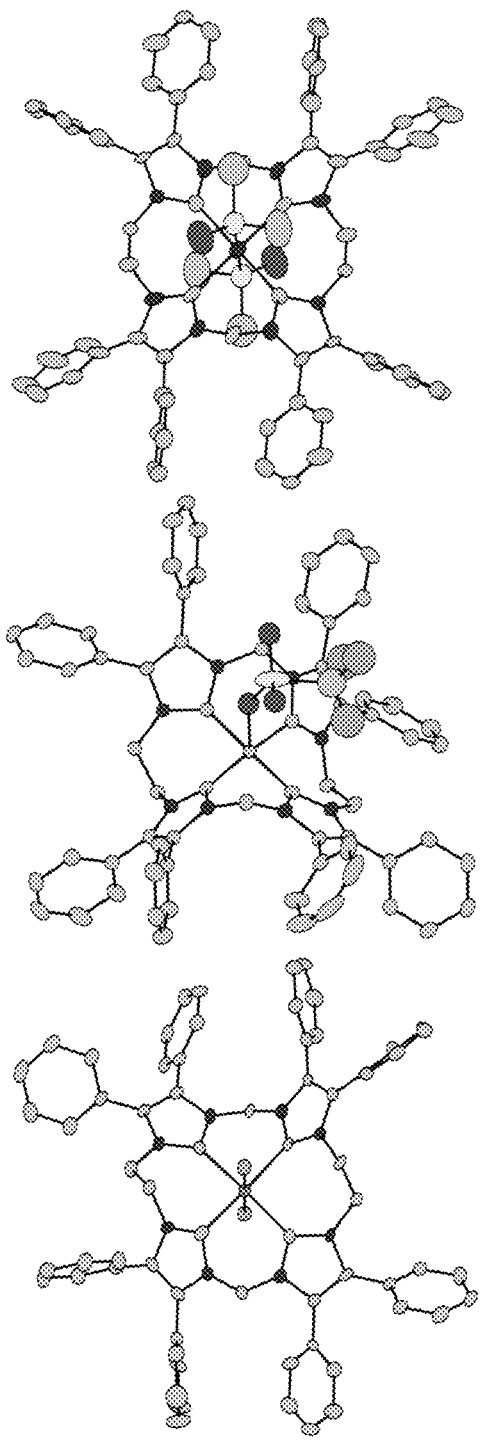
FIG. 9 shows X-ray crystal structures of $[(^{Me,Et}TC^{Ph})Ru(DMSO)_2](OTf)_2$ (6, top), $[(^{Me,Et}TC^{Ph})Co(OTf)](Otf)$ (7, middle), and $[(^{Me,Et}TC^{Ph})Cr(Cl)_2](PF_6)$ (8, bottom). Ellipsoids (50% probability) represent Ru, Co, Cr, N, C, S, O, F and Cl, respectively. Counteranions, solvent molecules and H atoms have been omitted for clarity.

To demonstrate that the transmetallation strategy was more general, the second row metal ruthenium was chosen. With Ru(DMSO)$_4$Cl$_2$ as the starting material, the tetracarbene complex, [($^{Me,Et}$TC$^{Ph}$)Ru(DMSO)$_2$](OTf)$_2$ (6 in Table 3) can be prepared in 40% yield. This diamagnetic complex is isostructural to [($^{Me,Et}$TC$^{Ph}$)Fe(NCCH$_3$)$_2$](PF$_6$)$_2$ (FIG. 9, top). However, unlike the iron analogue [($^{Me,Et}$TC$^{Ph}$)Fe(NCCH$_3$)$_2$](PF$_6$)$_2$), the macrocycle in [($^{Me,Et}$TC$^{Ph}$)Ru(DMSO)$_2$](OTf)$_2$ is more rigid in solution since a geminal AB splitting pattern is observed in the $^1$H NMR for the protons on the methylene position. Although the DMSO exchanges in solution, it is slow on the NMR time scale in comparison to [($^{Me,Et}$TC$^{Ph}$)Fe(NCCH$_3$)$_2$](PF$_6$)$_2$. Structurally [($^{Me,Et}$TC$^{Ph}$)Ru(DMSO)$_2$](OTf)$_2$ is similar to several other octahedral tetracarbenes of Ru$^{II}$.

To further pioneer the transmetallation of NHCs to first row metals, this reaction with cobalt and chromium salts was examined. In the cobalt case, the reaction yielded [($^{Me,Et}$TC$^{Ph}$)Co(OTf)](OTf) (7 in Table 3) where one of the triflates is bound to the cobalt (FIG. 9, middle). This five-coordinate complex can best be described as having a square pyramidal geometry about the cobalt center with trans C—Co—C bond angles of 169.8° and 177.3°. The triflate ligand remains bound in solution as evidenced by $^{19}$F NMR where two signals are observed: a sharp peak at −78.5 (free OTf) and a broad peak at ~121.3 (bound OTf). Unlike a 24-atom ringed macrocyclic tetracarbene complex that had been previously synthesized by Murphy and Spicer, this divalent cobalt complex has room for an additional apical ligand to bind to the metal center.

The final example of a first row metal tetracarbene that was examined was chromium. In this case, the transmetallation reagent [{($^{Me,Et}$TC$^{Ph}$)Ag}$_2$Ag$_2$](PF$_6$)$_4$ was non-innocent and actually behaved as an oxidant. By adding five equivalents of the metal instead of two equivalents used in the general methodology, the reaction yielded [($^{Me,Et}$TC$^{Ph}$)Cr(Cl)$_2$](PF$_6$) (8 in Table 3) cleanly (FIG. 9, bottom). ESI-MS characterization confirmed the trivalent oxidation state of the complex as m/z peaks at 336.15 ([($^{Me,Et}$TC$^{Ph}$)Cr]$^{3+}$), 521.66 ([($^{Me,Et}$TC$^{Ph}$)Cr(Cl)]$^{2+}$), and 1078.25 ([($^{Me,Et}$TC$^{Ph}$)Cr(Cl)$_2$]$^+$) were observed. Complex [($^{Me,Et}$TC$^{Ph}$)Cr(Cl)$_2$](PF$_6$) is the first example of a tetracarbene on chromium and just the second example of silver transmetallation of an NHC to a group 7 or earlier metal.

Figure 10:
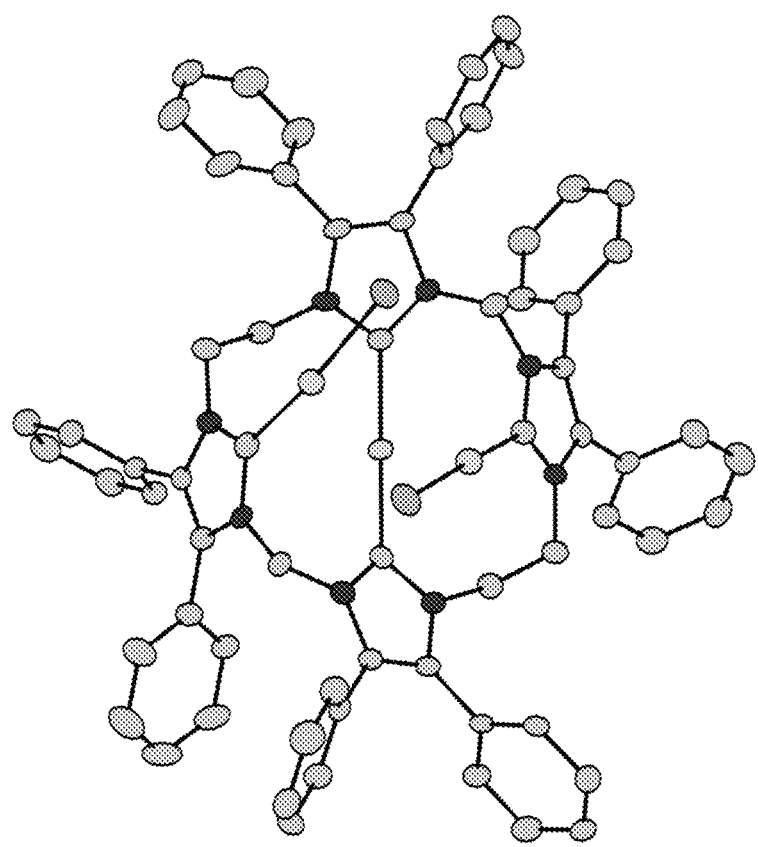
FIG. 10 shows the X-ray crystal structure of $[\{(^{Me,Et}TC^{Ph})Ag\}(AgCl)_2](OTf)$ (9). Ellipsoids (50% probability) represent Ag, N, C, and Cl, respectively. Counteranions, solvent molecules and H atoms have been omitted for clarity.

Given that the dimeric structure of [{($^{Me,Et}$TC$^{Ph}$)Ag}$_2$Ag$_2$](X)$_4$ is stable enough to observe the C—Ag coupling in the $^{13}$C NMR, one question is how does the dimeric species break up to perform the transmetallation? A serendipitous crystallization of an incomplete transmetallation reaction run with [{($^{Me,Et}$TC$^{Ph}$)Ag}$_2$Ag$_2$](OTf)$_4$ and Ru(DMSO)$_4$Cl$_2$ at room temperature provides some evidence (FIG. 10). The structure [{($^{Me,Et}$TC$^{Ph}$)Ag}(AgCl)$_2$](OTf) (9 in Table 3) shows that the dimer has broken up and that the bridging silvers now have bound chloride ligands which are trans to the bound carbene ligand. This result suggests that the intermolecular Ag—C bonds are the first one to break in the formation of the new M—C bonds.

As disclosed herein, the inventors have synthesized a dimeric silver NHC transmetallating reagent that reacts with a wide variety of divalent metal halides to give monomeric tetracarbene complexes. These silver complexes were characterized by $^1$H and $^{13}$C NMR spectroscopy, ESI-MS and single crystal X-ray diffraction, see below, all of which demonstrate that they are dimeric in the solid state and in solution. These silver reagents were demonstrated to transmetallate NHCs to five different metal salts from the first to third row on the period table in moderate to high yield. All of the metal tetracarbene complexes were structurally characterized by single crystal X-ray diffraction as well as ESI-MS and other spectroscopic techniques. The complexes formed for the three first row metals, chromium, iron and cobalt, are rare examples of silver NHC transmetallation to these metals. Given the importance of the few macrocyclic tetracarbenes that have been previously synthesized, this transmetallation strategy demonstrates that macrocyclic tetracarbenes can be prepared on metals across the periodic table.

General Considerations.

All reactions were performed under a dry nitrogen atmosphere with the use of either a glovebox or standard Schlenk techniques unless otherwise noted. Solvents were dried on an Innovative Technologies (Newburgport, Mass.) Pure Solv MD-7 Solvent Purification System and degassed by three freeze-pump-thaw cycles on a Schlenk line to remove $O_2$ prior to use. DMSO-$d_6$, acetonitrile-$d_3$, and chloroform-d were degassed by three freeze-pump-thaw cycles prior to drying over activated molecular sieves. These NMR solvents were then stored under $N_2$ in a glovebox. $(^{Me,Et}TC^{Ph})(OTf)_4$ and $(^{Me,Et}TC^{Ph})(I)_4$, were prepared as described previously. Characterization of $[(^{Me,Et}TC^{Ph})Fe(NCCH_3)_2](PF_6)_2$ is described in the Example below. All other reagents were purchased from commercial vendors and used without purification. $^1H$, $^{13}C\{^1H\}$, and $^{19}F$ NMR spectra were recorded at ambient temperature, unless otherwise noted, on a Varian Mercury 300 MHz or a Varian VNMRS 500 MHz narrow-bore broadband system. $^1H$ and $^{13}C$ NMR chemical shifts were referenced to the residual solvent. $^{19}F$ NMR chemical shifts are reported relative to an external standard of neat $CFCl_3$. The ESI/MS analyses were performed using a QSTAR Elite quadrupole time-of-flight (QTOF) mass spectrometer with an electrospray ionization source from AB Sciex (Concord, Ontario, Canada). Mass spectrometry sample solutions were prepared in acetonitrile. Infrared spectra were collected on a Thermo Scientific Nicolet iS10 with a Smart iTR accessory for attenuated total reflectance. UV-vis measurements were taken inside a dry glovebox on an Ocean Optics USB4000 UV-vis system with 1 cm path length quartz crystal cell. Cyclic voltammetry measurements were made inside a dry glovebox using a BAS Epsilon electrochemical analyzer with a platinum working electrode, platinum wire counter electrode, and $Ag/AgNO_3$ reference electrode. All potentials were measured versus an external standard of ferrocene.

Synthesis of $(^{Me,Et}TC^{Ph})(PF_6)_4$ (1b in scheme 4)

$(^{Me,Et}TC^{Ph})(I)_4$ (2.933 g, 1.997 mmol) and thallium hexafluorophosphate (2.790 g, 7.987 mmol) were added to a 100 mL round bottom flask followed by the addition of 10 mL of DMSO and 60 mL of acetonitrile. The slurry was allowed to stir for 24 h. The mixture was then filtered over Celite into a 500 mL filter flask. Water (200 mL) was added to the solution to yield a white precipitate that was collected on a 60 mL fine sintered glass frit as the pure white powder product (2.612 g, 85% yield). $^1H$ NMR (DMSO-$d_6$, 499.74 MHz): δ 10.04 (s, 4H), 7.44 (m, 16H), 7.26 (t, J=7.5 Hz, 8H), 7.17 (d, J=7.5 Hz, 8H), 6.98 (d, J=7.5 Hz, 8H), 6.63 (s, 4H), 4.67 (s, 8H). $^{13}C$ NMR (DMSO-$d_6$, 125.66 MHz): δ 136.7, 132.7, 132.5, 131.0, 130.6, 130.2, 129.4, 123.1, 122.2, 55.9, 46.8. $^{19}F$ NMR (DMSO-$d_6$, 470.39 MHz): δ −70.55 (d, J=705.6 Hz). IR (neat): 3145, 3067, 1560, 1445, 1372, 1336, 1278, 1254, 1241, 1226, 1177, 1027, 765 $cm^{-1}$. ESI/MS (m/z): $[M-PF_6]^+$ 1395.36, $[M-2PF_6]^{2+}$ 625.19, $[M-3PF_6]^{3+}$ 368.48. Anal. Calcd for $C_{66}H_{56}F_{24}N_8P_4$: C, 51.44; H, 3.66; N, 7.27. Found: C, 50.64; H, 3.78; N, 7.17.

Synthesis of $[(^{Me,Et}TC^{Ph})(H)_2Ag](OTf)_3$ (2 in Scheme 4)

$(^{Me,Et}TC^{Ph})(OTf)_4$ (0.256 g, 0.165 mmol) (1a in scheme 4) and silver(I) triflate (0.0420 g, 0.160 mmol) were added to a 20 mL vial wrapped in aluminum foil and dissolved in 15 mL of DMSO while stirring and heating to 90° C. After 10 min., triethylamine (0.165 g, 1.63 mmol) was added and allowed to stir for 24 h. The reaction mixture was cooled and brought out of the glovebox. The solution was added to a 200 mL beaker and quenched with 150 mL of water to yield a white precipitate. A white powder was collected on a 60 mL fine sintered glass frit. The product was dried by dissolving the white powder in methylene chloride (100 mL) followed by addition of anhydrous $MgSO_4$, and filtration over a 60 mL medium sintered glass frit to remove the $MgSO_4$. Volatiles were removed under reduced pressure to yield the pure white powder product (0.200 g, 80% yield). Single crystals suitable for single crystal X-ray diffraction can be grown via vapor diffusion of pentane into a solution of $[(^{Me,Et}TC^{Ph})(H)_2Ag]$ $(OTf)_3$ in methylene chloride. $^1H$ NMR ($CD_3CN$, 60° C., 499.74 MHz): δ 9.88 (s, 2H), 7.56 (m, 6H), 7.41 (m, 18H), 7.27 (m, 8H), 7.19 (d, J=7.5 Hz, 4H), 6.78 (d, J=13.5 Hz, 2H), 6.68 (d, J=6.5 Hz, 4H), 5.90 (d, J=14.0 Hz, 2H), 4.60 (dd, $J_1$=15.5 Hz, $J_2$=8.0 Hz, 2H), 4.44 (m, 4H), 4.31 (dd, $J_1$=15.5 Hz, $J_2$=4.5 Hz, 2H). $^{13}C$ NMR ($CD_3CN$, 60° C., 125.66 MHz): δ 178.38 ($J_{Ag-C}$=202.4 Hz), 138.37, 135.82, 134.41, 134.24, 132.66, 132.52, 132.39, 132.29, 132.14, 131.89, 131.42, 131.27, 130.49, 130.33, 130.31, 129.90, 127.42, 126.51, 125.05, 124.84, 122.37 (q, $J_{F-C}$=321.6 Hz), 59.87, 50.25, 50.10. $^{19}F$ NMR ($CD_3CN$, 470.39 MHz): δ −79.14. IR (neat) 3116, 3056, 2964, 1663, 1635, 1552, 1489, 1445, 1359, 1333, 1249, 1223, 1152, 1076, 1057, 1027, 930, 836, 760, 697, 661 $cm^{-1}$. ESI/MS (m/z): $[M-OTf]^+$1364.86, $[M-2OTf]^{2+}$607.24, $[M-H-3OTf]^{2+}$533.27, $[M-3OTf]^{3+}$355.19. Electrochemistry (vs. ferrocene in $CH_3CN$ with (TBA) ($PF_6$) as supporting electrolyte): −2181 mV (in.), −2387 mV (irr.). Anal. Calcd for $C_{67}H_{56}N_8O_9F_9Cl_2S_3Ag$ ($2CH_2Cl_2$): C, 52.57; H, 3.53; N, 7.01. Found: C, 53.44; H, 3.71; N, 7.25.

Synthesis of $[\{(^{Me,Et}TC^{Ph})Ag\}_2Ag_2](OTf)_4$ (3a in Scheme 4)

$(^{Me,Et}TC^{Ph})(OTf)_4$ (0.580 g, 0.373 mmol) (1a) and silver(I) triflate (0.190 g, 0.742 mmol) were added to a 20 mL vial wrapped in aluminum foil and dissolved in 15 mL of DMSO while stirring and heating to 90° C. After 10 min., triethylamine (0.165 g, 1.63 mmol) was added and allowed to stir for 24 h. The reaction mixture was cooled to rt and brought out of the glovebox. The solution was added to a 200 mL beaker and quenched with 150 mL of water to yield a white precipitate. A white powder was collected on a 60 mL fine sintered glass frit. The product was dried by dissolving the white powder in methylene chloride (100 mL) followed by addition of anhydrous $MgSO_4$, and filtration over a 60 mL medium sintered glass frit to remove the $MgSO_4$. Volatiles were removed under reduced pressure to yield the pure white powder product (0.534 g, 95% yield). Single crystals suitable for single crystal X-ray diffraction can be grown by layering an acetone solution of $[\{(^{Me,Et}TC^{Ph})Ag\}_2Ag_2](OTf)_4$ with water to give colorless needles. $^1$H NMR (CD$_3$CN, 499.74 MHz): δ 7.64 (t, J=7.0 Hz, 4H), 7.57 (t, J=7.0 Hz, 8H), 7.47 (t, J=7.5 Hz, 4H), 7.40 (t, J=7.0 Hz, 4H), 7.36 (t, J=7.5 Hz, 4H), 7.25 (t, J=7.5 Hz, 8H), 7.19 (m, 16H), 7.08 (s, 8H), 6.97 (d, J=8.0 Hz, 8H), 6.79 (m, 12H), 6.13 (m, 8H), 6.03 (d, J=15.0 Hz, 4H), 5.14 (m, 4H), 4.94 (m, 4H), 4.41 (t, J=13.0 Hz, 4H), 4.06 (d, J=14.0 Hz, 4H). $^{13}$C NMR (CD$_3$CN, 125.66 MHz): δ 183.18 ($^1$J$^{109}_{Ag-C}$=199.9 Hz, $^1$J$^{107}_{Ag-C}$=168.5 Hz), 176.96 ($^1$J$_{Ag-C}$=217.5 Hz, $^1$J$_{Ag-C}$=189.8 Hz), 136.92 (d, J$_{Ag-C}$=5.0 Hz), 135.74 (d, J$_{Ag-C}$=5.0 Hz), 135.21 (d, J$_{Ag-C}$=5.0 Hz), 133.82 (d, J$_{Ag-C}$=5.0 Hz), 132.15, 131.90, 131.86, 131.64, 131.62, 131.37, 131.29, 131.05, 130.53, 130.18, 130.05, 127.00, 126.42, 125.63, 125.55, 121.96 (q, J$_{F-C}$=320.4 Hz), 61.90, 51.12, 49.11. $^{19}$F NMR (CD$_3$CN, 470.39 MHz): δ –78.62. IR (neat): 2950, 2917, 2868, 2837, 1487, 1457, 1376, 1258, 1222, 1157, 1076, 1026, 973, 840, 763, 698 cm$^{-1}$. ESI/MS (m/z): [M–2OTf]$^{2+}$ 1321.10, [M–3OTf]$^{3+}$ 831.08, [M–4OTf]$^{4+}$ 586.07. Electrochemistry (vs. ferrocene in CH$_3$CN with (TBA)(PF$_6$) as supporting electrolyte): –1880 mV (rev.), –2490 mV (rev.). Anal. Calcd for C$_{136}$H$_{104}$N$_{16}$O$_{12}$F$_{12}$S$_4$Ag$_4$: C, 55.44; H, 3.69; N, 7.61. Found: C, 54.86; H, 3.89; N, 7.62.

Synthesis of [{($^{Me,Et}$TC$^{Ph}$)Ag}$_2$Ag$_2$](PF$_6$)$_4$ (3b)

($^{Me,Et}$TC$^{Ph}$)(PF$_6$)$_4$ (1.455 g, 0.944 mmol) (1b in scheme 4) and silver(I) hexafluorophosphate (0.477 g, 1.89 mmol) were added to a 20 mL vial wrapped in aluminum foil and dissolved in 15 mL of DMSO while stirring and heating to 90° C. After 10 min, triethylamine (0.477 g, 4.72 mmol) was added and allowed to stir for 48 h. The reaction mixture was cooled to rt and brought out of the glovebox. The solution was added to a 200 mL beaker and quenched with 150 mL of water to yield a white precipitate. The white powder was collected on a 60 mL fine sintered glass frit. The powder was then purified by dissolving in (40 mL) acetone in the sintered frit, filtering, and triturating with excess water (200 mL). The resulting fine powder was collected on a 60 mL fine sintered glass frit which yielded the pure white powder product (1.238 g, 90% yield). Single crystals suitable for X-ray diffraction can be grown by layering an acetone solution of [{($^{Me,Et}$TC$^{Ph}$)Ag}$_2$Ag$_2$](PF$_6$)$_4$ with water to give colorless needles. $^1$H NMR (CD$_3$CN, 499.74 MHz): δ 7.65 (t, J=7.5 Hz, 4H), 7.58 (t, J=6.5 Hz, 4H), 7.48 (t, J=8.0 Hz, 8H), 7.41 (t, J=7.5 Hz, 4H), 7.36 (t, J=8.0 Hz, 4H), 7.26 (t, J=8.0 Hz, 8H), 7.19 (m, 16H), 7.09 (s, 8H), 6.96 (d, J=7.0 Hz, 8H), 6.79 (s, 8H), 6.62 (d, J=14.5 Hz, 4H), 6.10 (d, J=7.5 Hz, 8H), 6.02 (d, J=13.5 Hz, 4H), 5.05 (td, J$_j$=13.5 Hz, J$_2$=3.5 Hz, 4H), 4.82 (dd, J$_j$=15.5 Hz, J$_2$=2.0 Hz, 4H), 4.44 (m, 4H), 4.03 (d, J=14.0 Hz, 4H). $^{13}$C NMR (CD$_3$CN, 125.66 MHz): δ 182.83 (J$^{109}_{Ag-C}$=214.9 Hz, J$^{107}_{Ag-C}$=181.0 Hz), 176.85 (J$^{109}_{Ag-C}$=218.7 Hz, J$^{107}_{Ag-C}$=188.5 Hz), 137.00 (d, J$_{Ag-C}$=5.8 Hz), 135.91 (d, J$_{Ag-C}$=5.3 Hz), 135.21 (d, J$_{Ag-C}$=5.3 Hz), 133.95 (d, J$_{Ag-C}$=5.0 Hz), 132.25, 131.99, 131.81, 131.71, 131.62, 131.47, 131.28, 131.11, 130.55, 130.20, 130.09, 126.91, 126.30, 125.53, 125.48, 61.85, 51.06, 49.16. $^{19}$F NMR (CD$_3$CN, 470.39 MHz): δ –72.81 (d, J=705.6 Hz). IR (neat): 2950, 2917, 2868, 2837, 1709, 1488, 1447, 1376, 1359, 1321, 1261, 1221, 1168, 1074, 1019, 827, 761, 739, 696 cm$^{-1}$. ESI/MS (m/z): [M–2PF$_6$]$^{2+}$ 1317.70, [M–3 PF$_6$]$^{3+}$ 829.82, [M–4 PF$_6$]$^{4+}$ 586.37. Electrochemistry (vs. ferrocene in CH$_3$CN with (TBA)(PF$_6$) as supporting electrolyte): –1848 mV (rev.), –2005 mV (rev.). Anal. Calcd for C$_{32}$H$_{104}$N$_{16}$F$_{24}$P$_4$Ag$_4$: C, 54.19; H, 3.58; N, 7.66. Found: C, 53.20; H, 3.83; N, 7.59.

General Transmetallation Reaction.

[{($^{Me,Et}$TC$^{Ph}$)Ag}$_2$Ag$_2$](X)$_4$ (3 in scheme 5) and the corresponding metal salt was added to a 20 mL vial followed by 4 mL of methylene chloride and 4 mL of tetrahydrofuran. The reaction mixture was stirred and heated at the designated temperature overnight. After allowing the reaction to cool to rt the silver halide was filtered away over Celite (except [($^{Me,Et}$TC$^{Ph}$)Ru(DMSO)$_2$](OTf)$_2$ (6 in Table 3)). The remainder of the work-up for each complex is described separately below.

Synthesis of [($^{Me,Et}$TC$^{Ph}$)Pt](OTf)$_2$ (4 in Table 3)

The general transmetallation reaction was followed using dichlorobis(benzonitrile)platinum(II) (0.0170 g, 0.0360 mmol) and [{($^{Me,Et}$TC$^{Ph}$)Ag}$_2$Ag$_2$](OTf)$_4$ (0.0500 g, 0.0170 mmol) at rt. The volatiles were removed from the resulting solution under reduced pressure to yield the pure white powder (0.0460 g, 93% yield). Crystals suitable for single crystal X-ray diffraction were obtained by vapor diffusing pentane into a solution of [($^{Me,Et}$TC$^{Ph}$)Pt](OTf)$_2$ in methylene chloride. $^1$H NMR (CD$_3$CN, 499.74 MHz): δ 7.43 (m, 12H), 7.35 (m, 12H), 7.22 (t, J=8.0 Hz, 8H), 7.12 (d, J=7.0 Hz, 8H), 5.98 (d, J=14.0 Hz, 2H), 5.78 (d, J=13.5 Hz, 2H), 4.74 (dd, J$_j$=15.0 Hz, J$_2$=8.0 Hz, 4H), 4.33 (dd, J$_1$=15.0 Hz, J$_2$=8.0 Hz, 4H). $^{13}$C NMR (125.66 MHz, CD$_3$CN): δ 161.28, 133.45, 132.27, 131.49, 130.92, 130.77, 129.94, 129.91, 127.55, 126.90, 122.11 (q, J$_{F-C}$=320.4 Hz), 118.28, 59.26, 48.01. $^{19}$F NMR (470.385 MHz, CD$_3$CN): δ –79.24. IR (neat) 3058, 2954, 1577, 1488, 1445, 1404, 1335, 1259, 1223, 1149, 1076, 1029, 925, 839, 764, 698 cm$^{-1}$. ESI/MS (m/z): [M–OTf]$^+$ 1301.38, [M–2OTf]$^{2+}$ 576.22; UV-vis (CH$_2$Cl$_2$) λ$_{max}$, nm (ε): 323 (21000). Anal. Calcd for C$_{70}$H$_{56}$N$_8$O$_6$F$_6$C$_{14}$S$_2$Pt (4.2 CH$_2$Cl$_2$): C, 51.89; H, 3.48; N, 6.92. Found: C, 51.34; H, 3.97; N, 7.00.

Synthesis of [($^{Me,Et}$TC$^{Ph}$)Fe(NCCH$_3$)$_2$](PF$_6$)$_2$ (5 in Table 3)

The general transmetallation reaction was followed using iron(II) iodide (0.0302 g, 0.0974 mmol) and [{($^{Me,Et}$TC$^{Ph}$)Ag}$_2$Ag$_2$](PF$_6$)$_4$ (0.143 g, 0.0487 mmol) at room temperature. Addition of acetonitrile followed by removal of volatiles under reduced pressure yielded the pure product as a red powder (0.124 g, 92% yield). The product can be crystallized by slow evaporation of diethyl ether into an acetonitrile solution of [($^{Me,Et}$TC$^{Ph}$)Fe(NCCH$_3$)$_2$](PF$_6$)$_2$ to afford red crystals.

Synthesis of [($^{Me,Et}$TC$^{Ph}$)Ru(DMSO)$_2$](OTf)$_2$ (6 in Table 3)

The general transmetallation reaction was followed using ruthenium(II) chloride tetradimethylsulfoxide (0.0570 g, 0.120 mmol) and [{($^{Me,Et}$TC$^{Ph}$)Ag}$_2$Ag$_2$](OTf)$_4$ (0.182 g, 0.0610 mmol). The reaction mixture was not filtered over Celite but instead over a 15 mL fine sintered glass frit. The solid was extracted with acetone (3×30 mL). The volatiles were removed under reduced pressure to yield white powdery product (0.075 g, 0.050 mmol, 40% yield). Crystals suitable for single crystal X-ray diffraction can be obtained by slow evaporation of a 50/50 v/v methanol and acetone solution of the 6 to yield colorless plates. $^1$H NMR (DMSO-d$_6$, 499.74 MHz) δ 7.38 (m, 12H), 7.30 (t, J=7.5 Hz, 4H), 7.25 (m, 8H), 7.16 (m, 16H), 6.28 (d, J=14.0 Hz, 2H), 6.04 (d, J=13.5 Hz, 2H), 4.52 (d, J=14.5 Hz, 4H), 4.42 (d, J=14.0 Hz, 4H). $^{13}$C NMR (DMSO-d$_6$, 125.66 MHz) δ 180.34, 134.43, 131.72, 130.94, 130.60, 129.44, 129.35, 128.74, 126.84, 125.78, 118.03, 56.55, 50.31. $^{19}$F NMR (DMSO-d$_6$, 470.39 MHz): δ –77.76. IR (neat) 3055, 2953, 1594, 1576, 1501, 1488, 1445, 1405, 1376, 1354, 1327, 1256, 1223, 1181, 1151, 1075, 1029, 925, 859, 839, 763, 697 cm$^{-1}$. ESI/MS (m/z): [M–OTf-DMSO]$^{2+}$ 1285.15, [M–2OTf]$^{2+}$ 607.11, [M–2OTf-DMSO]$^{2+}$ 568.11, [M–2OTf-2DMSO]$^{2+}$ 529.11. Electrochemistry (vs. ferrocene in DMSO with (TBA)(PF$_6$) as supporting electrolyte): +687 mV (in.). Anal. Calcd. for C$_{73}$H$_{66}$N$_8$O$_8$F$_6$C$_{12}$S$_4$Ru (6CH$_2$Cl$_2$): C, 55.16, H, 3.68, N, 7.17. Found: C, 55.17; H, 4.05; N, 7.88.

Synthesis of [($^{Me,Et}$TC$^{Ph}$)Co(OTf)]OTf (7 in Table 3)

The general transmetallation reaction was followed using cobalt(II) chloride (0.0060 g, 0.046 mmol) and [{($^{Me,Et}$TC$^{Ph}$)Ag}$_2$Ag$_2$](OTf)$_4$ (0.0660 g, 0.0200 mmol) at room temperature. The volatiles were removed from the resulting solution under reduced pressure and the remaining solids were dissolved into methylene chloride (2 mL). Purification was achieved by vapor diffusing pentane into this methylene chloride solution to yield light pink crystals that were suitable for single crystal X-ray diffraction (0.0400 g, 68% yield). $^{19}$F NMR (470.39 MHz, CD$_3$CN): δ −78.46 (s), −121.26 (br). IR (neat) 3056, 2924, 1603, 1594, 1488, 1444, 1388, 1341, 1325, 1275, 1247, 1223, 1150, 1074, 1027, 958, 923, 861, 845, 787, 763, 731, 697 cm$^{-1}$. UV-vis (CH$_2$Cl$_2$) λ$_{max}$, nm (ε): 376 (17000). ESI/MS (m/z): [M–OTf]$^+$ 1164.26, [M–2OTf]$^{2+}$ 507.68. Electrochemistry (vs. ferrocene in CH$_3$CN with (TBA)(PF$_6$) as supporting electrolyte): −1500 mV (rev.). Anal. Calcd for C$_{69}$H$_{54}$N$_8$O$_6$F$_6$Cl$_2$S$_2$Co (7CH$_2$Cl$_2$): C, 59.23; H, 3.89; N, 8.01. Found: C, 59.00; H, 3.72; N, 7.96.

Synthesis of [($^{Me,Et}$TC$^{Ph}$)Cr(Cl)$_2$]PF$_6$ (8 in Table 3)

The general transmetallation reaction was followed using chromium(II) chloride (0.0232 g, 0.0189 mmol) and [{($^{Me,Et}$TC$^{Ph}$)Ag}$_2$Ag$_2$](PF$_6$)$_4$ (0.111 g, 0.00378 mmol) at room temperature. The product was purified by crystallization via vapor diffusion of diethyl ether into the filtered reaction mixture to afford blue crystals (0.0532 g, 58% Yield). Crystals suitable for X-ray diffraction can be grown by slow evaporation of an acetonitrile solution of [($^{Me,Et}$TC$^{Ph}$)Cr(Cl)$_2$]PF$_6$ to yield blue plates. IR (neat) 2952, 1488, 1446, 1358, 1340, 1314, 1265, 1161, 1059, 1020, 836, 764, 735, 698 cm$^{-1}$. UV-vis (CH$_3$CN) λ$_{max}$, nm (ε): 570 (17). ESI/MS (m/z): [M–PF$_6$]$^+$ 1078.31, [M–PF$_6$—Cl]$^{2+}$ 521.67, [M–PF$_6$-2Cl]$^{3+}$ 336.12. Electrochemistry (vs. ferrocene in CH$_3$CN with (TBA)(PF$_6$) as supporting electrolyte): +1314 mV (in.), −1995 mV (irr.). Anal. Calcd for C$_{67}$H$_{54}$N$_8$F$_6$Cl$_4$PCr (8.CH$_2$Cl$_2$): C, 61.43; H, 4.15; N, 8.55. Found: C, 61.41; H, 4.20; N, 8.66.

Synthesis of [{($^{Me,Et}$TC$^{Ph}$)Ag}(AgCl)$_2$]OTf (9 in Table 3)

In one attempt to crystallize [($^{Me,Et}$TC$^{Ph}$)Ru(DMSO)$_2$](OTf)$_2$ by slow evaporation from a 50/50 v/v solution of methanol and acetone, [{($^{Me,Et}$TC$^{Ph}$)Ag}(AgCl)$_2$]OTf was co-crystallized as colorless block crystals. ESI/MS (m/z): [M–OTf]$^+$ 1351.09, [M–OTf-Cl]$^{2+}$ 658.05, [M–OTf-Cl—AgCl]$^{2+}$ 586.11.

X-ray Structure Determinations

X-ray diffraction measurements were performed on single crystals coated with Paratone oil and mounted on glass fibers or mounted on nylon CryoLoops (Hampton Research). Each crystal was frozen under a stream of N$_2$ while data were collected on a Bruker APEX diffractometer. Initial scans of each specimen were taken to obtain preliminary unit cell parameters and to assess the mosaicity (i.e. breadth of spots between frames) of the crystal to select the required frame width for data collection. For all cases frame widths of 0.5° were judged to be appropriate and full hemispheres of data were collected using the Bruker APEX2 software suite to carry out overlapping ϕ and ω scans at detector setting of 2θ=28°. Following data collection, reflections were sampled from all regions of the Ewald sphere to re-determine unit cell parameters for data integration. Following exhaustive review of collected frames the resolution of the dataset was judged, and, if necessary, regions of the frames where no coherent scattering was observed were removed from consideration for data integration using Bruker SAINTplus software. Data was integrated using a narrow frame algorithm and were subsequently corrected for absorption. Absorption corrections were performed for both samples using the SADABS program. Space group determination and tests for merohedral twinning were carried out using XPREP. In all cases, the highest possible space group was chosen.

Example 2

Synthesis and Characterization of Metal Bound Tetracarbene Catalysts

General Considerations

All reactions were performed under a dry nitrogen atmosphere with the use of either a dry box or standard Schlenk techniques. Solvents were dried on an Innovative Technologies (Newburgport, Mass.) Pure Solv MD-7 Solvent Purification System and degassed by three freezepump-thaw cycles on a Schlenk line to remove O$_2$ prior to use. DMSO-d6, acetonitrile-d3, benzene-d6, and chloroform-d were degassed by three freeze-pump-thaw cycles prior to drying over activated molecular sieves. These NMR solvents were then stored under N$_2$ in a glovebox. The compounds p-tolylazide, 1-azido-4-(trifluoromethyl)benzene, and ($^{Me,Et}$TC$^{Ph}$)(I)$_4$ were prepared as described previously (see Smith and Brown, *J. Am. Chem. Soc.* 1951, 73, 2438-2441; Abramovitch, et al., *J. Org. Chem.* 1972, 37, 2705; and Bass et al., *Organometallics* 2010, 29, 3235, all of which are specifically incorporated by reference in their entirety). All other reagents were obtained from commercial sources and used without purification. $^1$H, $^{13}$C {$^1$H}, and $^{19}$F NMR spectra were recorded at ambient temperature on a Varian Mercury 300 MHz or a Varian VNMRS 500 MHz narrow-bore broadband system. $^1$H and $^{13}$C NMR chemical shifts were referenced to the residual solvent. $^{19}$F NMR chemical shifts are reported relative to an external standard of neat CFCl$_3$. The DART analyses were performed using a JEOL AccuTOF-D time-of-flight (TOF) mass spectrometer with a DART (direct analysis in real time) ionization source from JEOL USA, Inc. (Peabody, Mass.). The ESI/MS analyses were performed using a QSTAR Elite quadrupole time-of-flight (QTOF) mass spectrometer with an electrospray ionization source from AB Sciex (Concord, Ontario, Canada). The GC/MS analyses were performed using a Hewlett Packard 6890 gas chromatography system with Hewlett Packard 5973 mass spectrometer. Mass spectrometry sample solutions of metal complexes were prepared in acetonitrile. Mass spectrometry sample solutions of organic compounds from catalysis reactions were prepared in hexanes. Infrared spectra were collected on a Thermo Scientific Nicolet iS10 with a Smart iTR accessory for attenuated total reflectance. UV-vis measurements were taken inside a dry glovebox on an Ocean Optics USB4000 UV-vis system with 1 cm path length quartz crystal cell. Cyclic voltammetry measurements were made inside a dry glovebox using a BAS Epsilon electrochemical analyzer with a platinum working electrode, platinum wire counter electrode, and Ag/AgNO$_3$ reference electrode. All potentials were measured versus an external standard of ferrocene. Carbon, hydrogen, and nitrogen analyses were obtained from Atlantic Microlab, Norcross, Ga.

Synthesis of [($^{Me,Et}$TC$^{Ph}$)Fe(NCCH$_3$)$_2$](PF$_6$)$_2$ ($^{Me,Et}$C$^{Ph}$)(I)$_4$ (2.570 g, 1.75 mmol) was added to tetrahydrofuran (20 mL) in a 100 mL round bottom flask and stirred for 10 min. Lithium di-isopropyl amide (0.562 g, 5.25 mmol) was dissolved in 5 mL of tetrahydrofuran and was added to the stirring ($^{Me,EtT}$C$^{Ph}$)(I)$_4$ mixture. After 3 min, iron(II) iodide (0.542 g, 1.75 mmol) which had been previously dissolved in tetrahydrofuran (20 mL) was added to the reaction mixture. After 10 min, additional solid lithium di-isopropyl amide (0.188 g, 1.75 mmol) was added to the reaction mixture and the mixture was allowed to stir for 24 h. All volatiles were removed under reduced pressure and diethyl ether (50 mL) was added to the crude solid and the ether mixture was stirred for 4 h. The slurry was then filtered over Celite and the filtered ether solution was discarded. The remaining solid in the flask was dissolved in methylene chloride (20 mL) and added to the top of the Celite filter flask and the solution was collected and the methylene chloride removed under reduced pressure. The resulting solid was dissolved in acetonitrile (50 mL) and thallium(I) hexafluorophosphate (1.223 g, 3.50 mmol) was added to the solution and allowed to stir for 4 h. The subsequent mixture was then filtered over Celite to S3 remove thallium iodide and the collected acetonitrile solution was reduced in volume to 1 mL. The pure product was crystallized via vapor diffusion of diethyl ether into the acetonitrile solution and the bright red crystals were collected after 5 d (0.279 g, 11.5% yield). $^1$H NMR (CD$_3$CN, 499.74 MHz): δ 7.41 (m, 8H), 7.33 (m, 16H), 7.21 (t, J=8.0 Hz, 8H), 7.12 (d, J=7.0 Hz, 8H), 5.96 (s, 4H), 4.44 (s, 8H). $^{13}$C NMR (CD$_3$CN, 125.66 MHz): δ 196.65, 135.44, 133.89, 132.39, 131.52, 130.39, 130.23, 129.83, 129.80, 129.10, 128.21, 57.44, 48.04. 19F NMR (CD$_3$CN, 282.3 MHz): δ −72.9 (d, J=706 Hz). IR (neat): 2975, 2255, 1979, 1602, 1488, 1445, 1365, 1181, 1075, 829, 769, 698 cm$^{-1}$. UV-vis (CH$_3$CN) λmax, nm (ε): 357 (33000), 435 (11000). ESI/MS (m/z): [M−PF$_6$]+ 1157.18, [M−2PF$_6$]$^{2+}$ 506.16. Electrochemistry (vs ferrocene in CH$_3$CN with [TBA][PF$_6$] as supporting electrolyte): Fe$^{III}$/Fe$^{II}$, +40 mV. Anal. Calcd for C$_{70}$H$_{58}$F$_{12}$N$_{10}$P$_2$Fe: C, 60.70; H, 4.22; N, 10.11. Found: C, 60.21; H, 4.14; N, 9.88.

General Catalytic Reaction

[($^{Me,Et}$TC$^{Ph}$)Fe(NCCH$_3$)$_2$](PF$_6$)$_2$ was added to a 20 mL vial (100 mL pressure vial for Table 3 entry 5 and 6) followed by the addition of the alkene. The reaction mixture was heated and stirred for 10 min. The aryl azide was then added to the reaction and allowed to stir at the designated temperature. Once aryl azide was no longer present (as determined by GC/MS) the mixture was removed from heat and [($^{Me,Et}$TC$^{Ph}$)Fe(NCCH$_3$)$_2$](PF$_6$)$_2$ was filtered away over Celite. [($^{Me,Et}$TC$^{Ph}$)Fe(NCCH$_3$)$_2$](PF$_6$)$_2$ can be recollected for re-use by adding acetonitrile to the filter and collecting the solution. Removal of the acetonitrile under reduced pressure gives [($^{Me,Et}$TC$^{Ph}$)Fe(NCCH$_3$)$_2$](PF$_6$)$_2$. The volatiles were removed under reduced pressure and, if needed, the product was purified by column chromatography on silica gel using a 9:1 ratio of hexanes to ethyl acetate as eluent.

Synthesis of 2-octyl-1-(p-tolyl)aziridine 0.1% catalyst loading: p-Tolyl azide (0.240 g, 1.81 mmol), 1-decene (7.410 g, 52.8 mmol), and [($^{Me,Et}$TC$^{Ph}$)Fe (NCCH$_3$)$_2$](PF$_6$)$_2$ (0.0025 g, 0.0018 mmol) were used in the General Catalytic Reaction described above yielding 0.312 g, 70.4%. 1% catalyst loading: p-Tolyl azide (0.103 g, 0.773 mmol), 1-decene (2.223 g, 15.8 mmol), and [($^{Me,Et}$TC$^{Ph}$)Fe (NCCH$_3$)$_2$](PF$_6$)$_2$ (0.0107 g, 0.0077 mmol) were used in the General Catalytic Reaction described above yielding 0.156 g, 82.1%. $^1$H NMR (CDCl$_3$, 499.74 MHz): δ 7.03 (d, J=7.5 Hz, 2H), 6.89 (d, J=7.0 Hz, 2H), 2.28 (s, 3H), 2.03 (m, 3H), 1.59 (m, 4H), 1.40 (m, $^2$H), 1.31 (m, 8H), 0.91 (t, J=6.0 Hz, 3H). $^{13}$C NMR (CDCl$_3$, 125.66 MHz): δ 152.77, 131.45, 129.51, 120.65, 40.33, 34.17, 33.41, 32.02, 29.74, 29.69, 29.42, 27.85, 22.80, 20.78, 14.24. GC/MS (m/z): 245.2. DART HR MS (m/z): [M+H]+246.2211 (found). C$_{17}$H$_{28}$N, 246.2222 (calcd).

Synthesis of 2-hexyl-1-(4-(trifluoromethyl)phenyl)aziridine 1-azido-4-(trifluoromethyl)-benzene (0.392 g, 2.09 mmol), 1-octene (3.575 g, 31.9 mmol), and [($^{Me,Et}$TC$^{Ph}$)Fe (NCCH$_3$)$_2$](PF$_6$)$_2$ (0.0029 g, 0.0021 mmol) were used in the General Catalytic Reaction described above yielding 0.212 g, 37.3%. $^1$H NMR (CDCl$_3$, 499.74 MHz): δ 7.47 (d, J=8.0 Hz, 2H), 7.03 (d, J=8.0 Hz, 2H), 2.13 (m, 2H), 2.09 (d, J=6.0 Hz, 1H), 1.58 (m, 4H), 1.41 (m, 2H), 1.34 (m, 4H), 0.92 (t, J=6.5 Hz, 3H). $^{13}$C NMR (CDCl$_3$, 125.66 MHz): δ 158.40, 126.27 (q, J=3.8 Hz), 124.60 (q, J=270.0 Hz), 124.19 (q, J=32.7 Hz), 120.83, 40.55, 34.23, 33.16, 31.97, 29.32, 27.71, 22.75, 14.18. 19F NMR (CDCl$_3$, 470.2 MHz): δ −61.7. GC/MS (m/z): 271.1. DART HR MS (m/z): [M+H]+272.1609 (found). C$_{15}$H$_{21}$F$_3$N, 272.1626 (calcd).

Synthesis of 9-(p-tolyl)-9-azabicyclo[6.1.0]nonane p-Tolyl azide (0.192 g, 1.44 mmol) and cis-cyclooctene (4.230 g, 38.4 mmol), and [($^{Me,Et}$TC$^{Ph}$)Fe(NCCH$_3$)$_2$](PF$_6$)$_2$ (0.0020 g, 0.0014 mmol) were used in the General S4 Catalytic Reaction described above yielding 0.302 g, 97.1%. $^1$H NMR (CDCl$_3$, 499.74 MHz): δ 7.02 (d, J=8.5 Hz, 2H), 6.88 (d, J=8.0 Hz, 2H), 2.32 (dd, J1=13.5 Hz, J2=2.5 Hz, 2H), 2.28 (s, 3H), 2.05 (d, J=9.5 Hz, 2H), 1.65 (m, 4H), 1.50 (m, 6H). $_{13}$C NMR (CDCl$_3$, 125.66 MHz): δ 153.08, 131.14, 129.41, 120.15, 43.73, 27.36, 27.20, 26.59, 20.77. GC/MS (m/z): 215.1. DART HR MS (m/z): [M+H]+216.1748 (found). C$_{15}$H$_{22}$N, 216.1752 (calcd).

Synthesis of 2,3-dipropyl-1-(p-tolyl)aziridine p-Tolyl azide (0.113 g, 0.852 mmol), trans-4-octene (3.705 g, 33.0 mmol), and [($^{Me,Et}$TC$^{Ph}$)Fe(NCCH$_3$)$_2$](PF$_6$)$_2$ (0.0118 g, 0.0085 mmol) were used in the General Catalytic Reaction described above yielding 0.055 g, 30%. $^1$H NMR (CDCl$_3$, 499.74 MHz): δ 7.02 (d, J=7.5 Hz, 2H), 6.80 (d, J=8.5 Hz, 2H), 2.28 (s, 3H), 2.03 (t, J=5.5 Hz, 2H), 1.62 (m, 2H), 1.53 (m, 4H), 1.10 (m, 2H), 0.96 (t, J=7.0 Hz, 6H) $^{13}$C NMR (CDCl$_3$, 125.66 MHz): δ 148.10, 130.91, 129.36, 120.95, 44.99, 33.29, 21.11, 20.80, 14.18. GC/MS (m/z): 217.2. DART HR MS (m/z): [M+H]+218.1901 (found). C$_5$H$_{24}$N, 218.1909 (calcd).

Synthesis of 1-methyl-7-(p-tolyl)-7-azabicyclo [4.1.0]heptane p-Tolyl azide (0.100 g, 0.751 mmol), 1-methyl-cyclohexene (4.055 g, 42.2 mol), and [($^{Me,Et}$TC$^{Ph}$)Fe(NCCH$_3$)$_2$] (PF$_6$)$_2$ (0.0104 g, 0.0075 mmol) were used in the General Catalytic Reaction described above yielding 0.059 g, 39%.

¹H NMR (CDCl₃, 499.74 MHz): δ 7.02 (d, J=7.5 Hz, 2H), 6.75 (d, J=6.5 Hz, 2H), 2.28 (s, 3H), 2.15 (m, 1H), 2.02 (m, 1H), 1.99 (m, 2H), 1.64 (m, 1H), 1.55 (m, 2H), 1.35 (m, 1H), 1.25 (m, 1H), 0.99 (s, 3H) ¹³C NMR (CDCl₃, 125.66 MHz): δ 148.74, 130.52, 129.27, 120.49, 44.17, 41.60, 32.41, 24.62, 21.16, 20.85, 20.81, 20.65. GC/MS (m/z): 201.1. DART HR MS (m/z): [M+H]+202.1594 (found). $C_{15}H_{22}N$, 202.1596 (calcd).

Synthesis of 2,2,3,3-tetramethyl-1-(p-tolyl)aziridine p-Tolyl azide (0.231 g, 1.73 mmol), 2,3-dimethyl-2-butene (3.540 g, 42.1 mmol), and [($^{Me,Et}$TC$^{Ph}$)Fe(NCCH₃)₂](PF₆)₂ (0.0024 g, 0.0017 mmol) were used in the General Catalytic Reaction described above yielding 0.067 g, 20%. ¹H NMR (CDCl₃, 499.74 MHz): δ 7.00 (d, J=8.0 Hz, 2H), 6.62 (d, J=8.0 Hz, 2H), 2.27 (s, 3H), 1.25 (s, 12H). 13C NMR (CDCl₃, 125.66 MHz): δ 145.46, 129.54, 129.24, 120.50, 44.14, 20.80, 20.55. GC/MS (m/z): 189.1. DART HR MS (m/z): [M+H]+190.1601 (found). $C_{13}H_{20}N$, 190.1596 (calcd).

Control Reactions.

Selected control reactions following the method of the General Catalytic Reaction were attempted but without [($^{Me,Et}$TC$^{Ph}$)Fe(NCCH₃)₂](PF₆)₂. These reactions either gave lower yields for aziridines or almost no isolable aziridine. Two example cases are shown. 2-octyl-1-(ptolyl)aziridine. p-Tolyl azide (0.096 g, 0.72 mmol) and 1-decene (1.853 g, 13.2 mmol) were used in the General Catalytic Reaction described above yielding 0.078 g, 43% yield. 1-methyl-7-(p-tolyl)-7-azabicyclo[4.1.0]heptane. p-Tolyl azide (0.203 g, 1.53 mmol) and 1-methylcyclohexene (4.055 g, 42.2 mol) were used in the General Catalytic Reaction described above yielding 0.007 g, 2% yield.

X-ray Structure Determinations.

X-ray diffraction measurements were performed on single crystals coated with Paratone oil and mounted on glass fibers. Each crystal was frozen under a stream of N₂ while data were collected on a Bruker APEX diffractometer. A matrix scan using at least 12 centered reflections was used to determine initial lattice parameters. Reflections were merged and corrected for Lorenz and polarization effects, scan speed, and background using SAINT 4.05. Absorption corrections, including odd and even ordered spherical harmonics were performed using SADABS, if necessary. Space group assignments were based upon systematic S5 absences, E statistics, and successful refinement of the structure. The structures were solved by direct methods with the aid of successive difference Fourier maps, and were refined against all data using the SHELXTL 5.0 software package. The structure of 2 has two types of disorder. First, one of the PF₆ counteranions has fluorine atoms that are split over multiple positions to improve the electron density map. Second, one of the solvent positions is disordered between one ether molecule and two acetonitrile molecules. This was modeled including each of these moieties (1CH₃CH₂OCH₂CH₃ or 2CH₃CN) at 50% weighting. All of the solvent molecules were refined isotropically.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A compound having the formula:

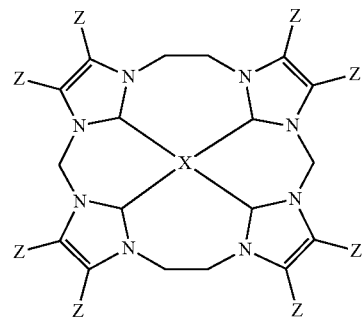

where X is a group 6, 7, or 8 metal, and wherein Z is a hydrogen, alkyl, aryl or organic group, wherein the alkyl, aryl or organic group is optionally and independently substituted at any or all positions.

2. The compound of claim 1, wherein the compound has the formula:

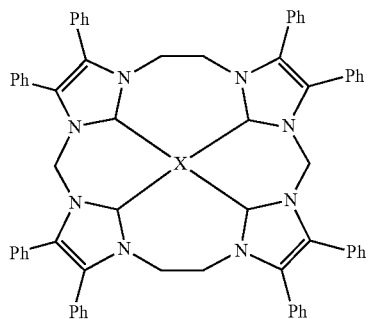

wherein X is a group 6, 7, or 8 metal, and wherein optionally the phenyl (Ph) groups are independently substituted.

3. The compound of claim 1, wherein X is a group 8 metal selected from the group consisting of Fe, Ru, and Os.

4. The compound of claim 3, wherein the metal is Fe.

5. The compound of claim 4, having the formula:

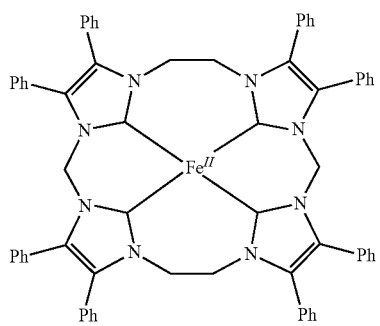

6. A method of making a transmetallating agent, comprising:
contacting ($^{Me,Et}$TC$^{Ph}$)(X)₄, where X is OTf with Ag(OTf) and NEt₃ in DMSO to produce the transmetallating agent

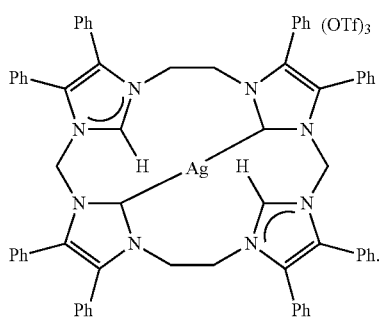

7. A method of making a metal bound tetracarbene catalyst, comprising:
   contacting a transmetallating reagent, comprising [{($^{Me,Et}TC^{Ph}$)Ag}$_2$Ag$_2$](x)$_4$, where X is a counter ion with a group 6, 7, 8, 9, or 10 metal salt in the presence of a solvent comprising a mixture of THF and CH$_2$Cl$_2$.

8. A method of making a metal bound tetracarbene catalyst, comprising:
   contacting a transmetallating reagent, comprising [{($^{Me,Et}TC^{Ph}$)Ag}$_2$Ag$_2$](X)$_4$, where X is a counter ion with a group 6, 7, 8, 9, or 10 metal salt in the presence of an organic solvent comprising tetrahydrofuran (THF).

9. A method of catalytic alkene aziridination, the method comprising:
   treating an alkene with an optionally substituted alkyl or aryl azide in the presence of the metal bound tetracarbene catalyst of claim 1.

10. The method of claim 9, wherein the metal bound tetracarbene catalyst is [($^{Me,Et}TC^{Ph}$)Fe(NCCH$_3$)$_2$(PF$_6$)$_2$.

11. The method of claim 9, wherein the alkene is selected from the group consisting of aromatic alkene, di-substituted alkene, tri-substituted alkene, tetra-substituted alkene, cis-alkene, trans-alkene, and cyclic-alkene.

12. A method of making a metal bound tetracarbene catalyst, comprising:
   contacting a tetraimidazolium precursor ($^{Me,Et}TC^{Ph}$)(I)$_4$, with a strong base to deprotonate the tetraimidazolium precursor, thereby forming a deprotonated tetraimidazolium precursor, wherein the phenyl groups of the tetraimidazolium precursor are optionally substituted; and
   contacting the deprotonated tetraimidazolium precursor with a solution comprising a group 6, 7, 8, or 10 metal.

13. The method of claim 12, further comprising:
   contacting the deprotonated tetraimidazolium precursor with thallium hexafluorophosphate or OTf in acetonitrile, THF and/or DMSO thereby forming a metal bound tetracarbene catalyst having the formula [($^{Me,Et}TC^{Ph}$)X(z)$_2$](Y)$_2$, where X is the group 6, 7, 8, or 10 metal, Z is the acetonitrile, THF and/or DMSO and Y is hexafluorophosphate or OTf.

14. The method of claim 12, wherein the strong base comprises lithium diisopropylamide (LiN$^i$Pr$_2$).

15. A method of making a transmetallating agent, comprising: contacting ($^{Me,Et}TC^{Ph}$)(X)$_4$, where X is OTf or PF$_6$ with Ag(X$^2$) where (X$^2$ is OTf or PF$_6$) and NEt$_3$ in DMSO to produce the transmetallating agent

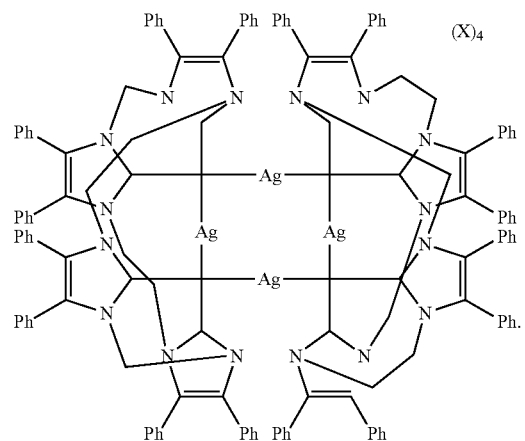

16. The method of claim 9, wherein the alkene is selected from the group consisting of non-aromatic alkene and non-cyclic alkene.

* * * * *